US011220682B2

(12) United States Patent
Lee et al.

(10) Patent No.: US 11,220,682 B2
(45) Date of Patent: Jan. 11, 2022

(54) INTRODUCING METHOD OF L-DIHYDROXYPHENYLALANINE IN TARGET PROTEIN

(71) Applicant: SOGANG UNIVERSITY RESEARCH & BUSINESS DEVELOPMENT FOUNDATION, Seoul (KR)

(72) Inventors: Hyun Soo Lee, Gimpo-si (KR); Sanggil Kim, Goyang-si (KR)

(73) Assignee: SOGANG UNIVERSITY RESEARCH & BUSINESS DEVELOPMENT FOUNDATION, Seoul (KR)

(*) Notice: Subject to any disclaimer, the term of this patent is extended or adjusted under 35 U.S.C. 154(b) by 697 days.

(21) Appl. No.: 16/034,711

(22) Filed: Jul. 13, 2018

(65) Prior Publication Data

US 2019/0017043 A1 Jan. 17, 2019

(30) Foreign Application Priority Data

Jul. 13, 2017 (KR) ........................ 10-2017-0088940

(51) Int. Cl.

| | |
|---|---|
| ***C12N 15/10*** | (2006.01) |
| ***C12N 15/74*** | (2006.01) |
| ***A61K 47/62*** | (2017.01) |
| ***A61K 47/42*** | (2017.01) |
| ***C12N 15/67*** | (2006.01) |
| ***A61K 47/64*** | (2017.01) |
| ***C12N 15/62*** | (2006.01) |

(52) U.S. Cl.

CPC ............ *C12N 15/102* (2013.01); *A61K 47/42* (2013.01); *A61K 47/62* (2017.08); *A61K 47/64* (2017.08); *C12N 15/62* (2013.01); *C12N 15/67* (2013.01); *C12N 15/74* (2013.01)

(58) Field of Classification Search

CPC ...... C12N 15/102; C12N 15/62; C12N 15/67; C12N 15/74; A61K 47/62; A61K 47/64; A61K 47/42

See application file for complete search history.

(56) References Cited

U.S. PATENT DOCUMENTS

| | | | | |
|---|---|---|---|---|
| 10,501,734 B2 * | 12/2019 | Isaacs | .................. | C12Y 601/01 |
| 2003/0082575 A1 * | 5/2003 | Schultz | ................ | C12P 13/005 435/6.14 |

FOREIGN PATENT DOCUMENTS

| | | | |
|---|---|---|---|
| JP | 5894535 | 3/2016 | |
| KR | 100571937 | 4/2006 | |
| WO | WO-2005038002 A2 * | 4/2005 | .............. C12N 9/93 |

OTHER PUBLICATIONS

Ayyadurai, N., Saravanan Prabhu, N., Deepankumar, K., Lee, S.-G., Jeong, H.-H., Lee, C.-S. and Yun, H. (2011), Development of a Selective, Sensitive, and Reversible Biosensor by the Genetic Incorporation of a Metal-Binding Site into Green Fluorescent Protein. Angew. Chern. Int. Ed., 50: 6534-6537. (Year: 2011).*

(Continued)

*Primary Examiner* — Kevin K Hill
*Assistant Examiner* — Anjeanette Roberts
(74) *Attorney, Agent, or Firm* — Cantor Colburn LLP

(57) ABSTRACT

Provided is a method of genetically incorporating an L-dihydroxyphenylalanine in a target protein.

6 Claims, 8 Drawing Sheets

Specification includes a Sequence Listing.

L-DOPA

TAG

TPL emGFP

DOPA-RS2 tRNA

(56) References Cited

OTHER PUBLICATIONS

Alfonta, L., Zhang, Z., Uryu, S., Loo, J. A., & Schultz, P. G. (2003). Site-specific incorporation of a redox-active amino acid into proteins. Journal of the American Chemical Society, 125(48), 14662-14663. (Year: 2003).*

Kim, et al., Genetic incorporation of L-dihydroxyphenylalanine (DOPA) biosynthesized by a tyrosine phenol-lyase, Chem. Commun., 2018, pp. 3002-3005.

Park, et al., Production of L-DOPA(3,4-Dihydroxyphenyl-L-alanine) from Benzene by Using a Hybrid Pathway, Biotechnology and Bioengineering, 1998, pp. 339-343.

* cited by examiner

SEQUENCE LISTING

<160> NUMBER OF SEQ ID NOS: 11

<210> SEQ ID NO 1
<211> LENGTH: 921
<212> TYPE: DNA
<213> ORGANISM: Artificial Sequence
<220> FEATURE:
<223> OTHER INFORMATION: Artificial DOPA_RS-1 DNA Sequence

<400> SEQUENCE: 1

```
atggacgaat ttgaaatgat aaagagaaac acatctgaaa ttatcagcga ggaagagtta     60

agagaggttt tagaaaaaga tgaaaagtct gctcttatag gttttgaacc aagtggtaaa    120

atacatttag ggcattatct ccaaataaaa aagatgattg atttacaaaa tgctggattt    180

gatataatta tattgttgtc tgatttaaat gcctatttaa accagaaagg agagttggat    240

gagattagaa aaatagggga ttataacaaa aaagtttttg aagcaatggg gttaaaggca    300

aaatatgttt atggaagtga attccagctt gataaggatt atacactgaa tgtctataga    360

ttggctttaa aaactacctt aaagagagca agaaggagta tggaacttat agcaagagag    420

gatgaaaatc caaaggttgc tgaagttatc tatccaataa tgcaggttaa tgatattcat    480

tatttaggcg tcgatgttaa cgttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921
```

<210> SEQ ID NO 2
<211> LENGTH: 921
<212> TYPE: DNA
<213> ORGANISM: Artificial Sequence
<220> FEATURE:
<223> OTHER INFORMATION: Artificial DOPA_RS-2 DNA Sequence

<400> SEQUENCE: 2

```
atggacgaat ttgaaatgat aaagagaaac acatctgaaa ttatcagcga ggaagagtta     60

agagaggttt tagaaaaaga tgaaaagtct gctcttatag gttttgaacc aagtggtaaa    120

atacatttag ggcattatct ccaaataaaa aagatgattg atttacaaaa tgctggattt    180

gatataatta tattgttgtc tgatttaaat gcctatttaa accagaaagg agagttggat    240

gagattagaa aaatagggga ttataacaaa aaagtttttg aagcaatggg gttaaaggca    300

aaatatgttt atggaagtga attccagctt gataaggatt atacactgaa tgtctataga    360

ttggctttaa aaactacctt aaagagagca agaaggagta tggaacttat agcaagagag    420

gatgaaaatc caaaggttgc tgaagttatc tatccaataa tgcaggttaa tgatattcat    480

tatttaggcg tcgatgttct ggttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780
```

```
tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921
```

<210> SEQ ID NO 3
<211> LENGTH: 306
<212> TYPE: PRT
<213> ORGANISM: Artificial Sequence
<220> FEATURE:
<223> OTHER INFORMATION: Artificial DOPA_RS-1 Sequence

<400> SEQUENCE: 3

```
Met Asp Glu Phe Glu Met Ile Lys Arg Asn Thr Ser Glu Ile Ile Ser
1               5                   10                  15

Glu Glu Glu Leu Arg Glu Val Leu Glu Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ser Asp Leu Asn Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Asn Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 4

```
<211> LENGTH: 306
<212> TYPE: PRT
<213> ORGANISM: Artificial Sequence
<220> FEATURE:
<223> OTHER INFORMATION: Artificial DOPA_RS-2 Sequence

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Glu Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ser Asp Leu Asn Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Leu Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 5
<211> LENGTH: 77
<212> TYPE: DNA
<213> ORGANISM: Artificial Sequence
<220> FEATURE:
<223> OTHER INFORMATION: Artificial aa-tRNA Sequence

<400> SEQUENCE: 5

ccggcggtag ttcagcaggg cagaacggcg gactctaaat ccgcatggca ggggttcaaa     60
```

```
tcccctccgc cggacca                                                 77


<210> SEQ ID NO 6
<211> LENGTH: 6124
<212> TYPE: DNA
<213> ORGANISM: Artificial Sequence
<220> FEATURE:
<223> OTHER INFORMATION: Artificial pEvol_DOPA-RS_1 Sequence

<400> SEQUENCE: 6

tcctgaaaat ctcgataact caaaaaatac gcccggtagt gatcttattt cattatggtg     60

aaagttggaa cctcttacgt gccgatcaac gtctcatttt cgccaaaagt tggcccaggg    120

cttcccggta tcaacaggga caccaggatt tatttattct gcgaagtgat cttccgtcac    180

aggtatttat tcggcgcaaa gtgcgtcggg tgatgctgcc aacttactga tttagtgtat    240

gatggtgttt ttgaggtgct ccagtggctt ctgtttctat cagctgtccc tcctgttcag    300

ctactgacgg ggtggtgcgt aacggcaaaa gcaccgccgg acatcagcgc tagcggagtg    360

tatactggct tactatgttg gcactgatga gggtgtcagt gaagtgcttc atgtggcagg    420

agaaaaaagg ctgcaccggt gcgtcagcag aatatgtgat acaggatata ttccgcttcc    480

tcgctcactg actcgctacg ctcggtcgtt cgactgcggc gagcggaaat ggcttacgaa    540

cggggcggag atttcctgga agatgccagg aagatactta acagggaagt gagagggccg    600

cggcaaagcc gtttttccat aggctccgcc cccctgacaa gcatcacgaa atctgacgct    660

caaatcagtg gtggcgaaac ccgacaggac tataaagata ccaggcgttt ccccctggcg    720

gctccctcgt gcgctctcct gttcctgcct ttcggtttac cggtgtcatt ccgctgttat    780

ggccgcgttt gtctcattcc acgcctgaca ctcagttccg ggtaggcagt tcgctccaag    840

ctggactgta tgcacgaacc ccccgttcag tccgaccgct gcgccttatc cggtaactat    900

cgtcttgagt ccaacccgga aagacatgca aaagcaccac tggcagcagc cactggtaat    960

tgatttagag gagttagtct tgaagtcatg cgccggttaa ggctaaactg aaaggacaag   1020

ttttggtgac tgcgctcctc caagccagtt acctcggttc aaagagttgg tagctcagag   1080

aaccttcgaa aaaccgccct gcaaggcggt tttttcgttt tcagagcaag agattacgcg   1140

cagaccaaaa cgatctcaag aagatcatct tattaatcag ataaaatatt tctagatttc   1200

agtgcaattt atctcttcaa atgtagcacc tgaagtcagc cccatacgat ataagttgta   1260

attctcatgt ttgacagctt atcatcgata agcttggtac ccaattatga caacttgacg   1320

gctacatcat tcactttttc ttcacaaccg gcacggaact cgctcgggct ggccccggtg   1380

catttttaa atacccgcga gaaatagagt tgatcgtcaa aaccaacatt gcgaccgacg    1440

gtggcgatag gcatccgggt ggtgctcaaa agcagcttcg cctggctgat acgttggtcc   1500

tcgcgccagc ttaagacgct aatccctaac tgctggcgga aaagatgtga cagacgcgac   1560

ggcgacaagc aaacatgctg tgcgacgctg gcgatatcaa aattgctgtc tgccaggtga   1620

tcgctgatgt actgacaagc ctcgcgtacc cgattatcca tcggtggatg gagcgactcg   1680

ttaatcgctt ccatgcgccg cagtaacaat tgctcaagca gatttatcgc cagcagctcc   1740

gaatagcgcc cttccccttg cccggcgtta atgatttgcc caaacaggtc gctgaaatgc   1800

ggctggtgcg cttcatccgg gcgaaagaac cccgtattgg caaatattga cggccagtta   1860

agccattcat gccagtaggc gcgcggacga aagtaaaccc actggtgata ccattcgcga   1920

gcctccggat gacgaccgta gtgatgaatc tctcctggcg ggaacagcaa aatatcactc   1980
```

-continued

```
ggtcggcaaa caaattctcg tccctgattt ttcaccaccc cctgaccgcg aatggtgaga   2040
ttgagaatat aacctttcat tcccagcggt cggtcgataa aaaaatcgag ataaccgttg   2100
gcctcaatcg gcgttaaacc cgccaccaga tgggcattaa acgagtatcc cggcagcagg   2160
ggatcatttt gcgcttcagc catacttttc atactcccgc cattcagaga agaaaccaat   2220
tgtccatatt gcatcagaca ttgccgtcac tgcgtctttt actggctctt ctcgctaacc   2280
aaaccggtaa ccccgcttat taaaagcatt ctgtaacaaa gcgggaccaa agccatgaca   2340
aaaacgcgta acaaaagtgt ctataatcac ggcagaaaag tccacattga ttatttgcac   2400
ggcgtcacac tttgctatgc catagcattt ttatccataa gattagcgga tcctacctga   2460
cgctttttat cgcaactctc tactgtttct ccatacccgt ttttttgggc taacaggagg   2520
aattagatct atggacgaat ttgaaatgat aaagagaaac acatctgaaa ttatcagcga   2580
ggaagagtta agagaggttt tagaaaaaga tgaaaagtct gctcttatag gttttgaacc   2640
aagtggtaaa atacatttag ggcattatct ccaaataaaa aagatgattg atttacaaaa   2700
tgctggattt gatataatta tattgttgtc tgatttaaat gcctatttaa accagaaagg   2760
agagttggat gagattagaa aaatagggga ttataacaaa aaagtttttg aagcaatggg   2820
gttaaaggca aaatatgttt atggaagtga attccagctt gataaggatt atacactgaa   2880
tgtctataga ttggctttaa aaactacctt aaagagagca agaaggagta tggaacttat   2940
agcaagagag gatgaaaatc caaaggttgc tgaagttatc tatccaataa tgcaggttaa   3000
tgatattcat tatttaggcg tcgatgttaa cgttggaggg atggagcaga gaaaaataca   3060
catgttagca agggagcttt taccaaaaaa ggttgtttgt attcacaacc ctgtcttaac   3120
gggtttggat ggagaaggaa agatgagttc ttcaaaaggg aattttatag ctgttgatga   3180
ctctccagaa gagattaggg ctaagataaa gaaagcatac tgcccagctg gagttgttga   3240
aggaaatcca ataatggaga tagctaaata cttccttgaa tatcctttaa ccataaaaag   3300
gccagaaaaa tttggtggag atttgacagt taatagctat gaggagttag agagtttatt   3360
taaaaataag gaattgcatc caatggattt aaaaaatgct gtagctgaag aacttataaa   3420
gattttagag ccaattagaa agagattata agtcgaccat catcatcatc atcattgagt   3480
ttaaacggtc tccagcttgg ctgttttggc ggatgagaga agattttcag cctgatacag   3540
attaaatcag aacgcagaag cggtctgata aaacagaatt tgcctggcgg cagtagcgcg   3600
gtggtcccac ctgaccccat gccgaactca gaagtgaaac gccgtagcgc cgatggtagt   3660
gtggggtctc cccatgcgag agtagggaac tgccaggcat caaataaaac gaaaggctca   3720
gtcgaaagac tgggccttgt ttgtgagctc ccggtcatca atcatcccca taatccttgt   3780
tagattatca attttaaaaa actaacagtt gtcagcctgt cccgctttaa tatcatacgc   3840
cgttatacgt tgtttacgct ttgaggaatc ccatatggac gaatttgaaa tgataaagag   3900
aaacacatct gaaattatca gcgaggaaga gttaagagag gttttagaaa aagatgaaaa   3960
gtctgctctt ataggttttg aaccaagtgg taaaatacat ttagggcatt atctccaaat   4020
aaaaaagatg attgatttac aaaatgctgg atttgatata attatattgt tgtctgattt   4080
aaatgcctat ttaaaccaga aaggagagtt ggatgagatt agaaaaatag gggattataa   4140
caaaaaagtt tttgaagcaa tggggttaaa ggcaaaatat gtttatggaa gtgaattcca   4200
gcttgataag gattatacac tgaatgtcta tagattggct ttaaaaacta ccttaaagag   4260
agcaagaagg agtatggaac ttatagcaag agaggatgaa aatccaaagg ttgctgaagt   4320
tatctatcca ataatgcagg ttaatgatat tcattattta ggcgtcgatg ttaacgttgg   4380
```

-continued agggatggag cagagaaaaa tacacatgtt agcaagggag cttttaccaa aaaaggttgt 4440
ttgtattcac aaccctgtct taacgggttt ggatggagaa ggaaagatga gttcttcaaa 4500
agggaatttt atagctgttg atgactctcc agaagagatt agggctaaga taaagaaagc 4560
atactgccca gctggagttg ttgaaggaaa tccaataatg gagatagcta aatacttcct 4620
tgaatatcct ttaaccataa aaaggccaga aaaatttggt ggagatttga cagttaatag 4680
ctatgaggag ttagagagtt tatttaaaaa taaggaattg catccaatgg atttaaaaaa 4740
tgctgtagct gaagaactta taaagatttt agagccaatt agaaagagat tataactgca 4800
gtttcaaacg ctaaattgcc tgatgcgcta cgcttatcag gcctacatga tctctgcaat 4860
atattgagtt tgcgtgcttt tgtaggccgg ataaggcgtt cacgccgcat ccggcaagaa 4920
acagcaaaca atccaaaacg ccgcgttcag cggcgttttt tctgcttttc ttcgcgaatt 4980
aattccgctt cgcaacatgt gagcaccggt ttattgacta ccggaagcag tgtgaccgtg 5040
tgcttctcaa atgcctgagg ccagtttgct caggctctcc ccgtggaggt aataattgac 5100
gatatgatca gtgcacggct aactaagcgg cctgctgact ttctcgccga tcaaaaggca 5160
ttttgctatt aagggattga cgagggcgta tctgcgcagt aagatgcgcc ccgcattccg 5220
gcggtagttc agcagggcag aacggcggac tctaaatccg catggcaggg gttcaaatcc 5280
cctccgccgg accaaattcg aaaagcctgc tcaacgagca ggcttttttg catgctcgag 5340
cagctcaggg tcgaatttgc tttcgaattt ctgccattca tccgcttatt atcacttatt 5400
caggcgtagc accaggcgtt taagggcacc aataactgcc ttaaaaaaat tacgccccgc 5460
cctgccactc atcgcagtac tgttgtaatt cattaagcat tctgccgaca tggaagccat 5520
cacagacggc atgatgaacc tgaatcgcca gcggcatcag caccttgtcg ccttgcgtat 5580
aatatttgcc catggtgaaa acgggggcga agaagttgtc catattggcc acgtttaaat 5640
caaaactggt gaaactcacc cagggattgg ctgagacgaa aaacatattc tcaataaacc 5700
ctttagggaa ataggccagg ttttcaccgt aacacgccac atcttgcgaa tatatgtgta 5760
gaaactgccg gaaatcgtcg tggtattcac tccagagcga tgaaaacgtt tcagtttgct 5820
catggaaaac ggtgtaacaa gggtgaacac tatcccatat caccagctca ccgtctttca 5880
ttgccatacg gaattccgga tgagcattca tcaggcgggc aagaatgtga ataaaggccg 5940
gataaaactt gtgcttattt ttctttacgg tctttaaaaa ggccgtaata tccagctgaa 6000
cggtctggtt ataggtacat tgagcaactg actgaaatgc ctcaaaatgt tctttacgat 6060
gccattggga tatatcaacg gtggtatatc cagtgatttt tttctccatt ttagcttcct 6120
tagc 6124

<210> SEQ ID NO 7
<211> LENGTH: 6124
<212> TYPE: DNA
<213> ORGANISM: Artificial Sequence
<220> FEATURE:
<223> OTHER INFORMATION: Artificial pEvol_DOPA-RS_2 Sequence

<400> SEQUENCE: 7
tcctgaaaat ctcgataact caaaaaatac gcccggtagt gatcttattt cattatggtg 60
aaagttggaa cctcttacgt gccgatcaac gtctcatttt cgccaaaagt tggcccaggg 120
cttcccggta tcaacaggga caccaggatt tatttattct gcgaagtgat cttccgtcac 180
aggtatttat tcggcgcaaa gtgcgtcggg tgatgctgcc aacttactga tttagtgtat 240

-continued

```
gatggtgttt ttgaggtgct ccagtggctt ctgtttctat cagctgtccc tcctgttcag    300
ctactgacgg ggtggtgcgt aacggcaaaa gcaccgccgg acatcagcgc tagcggagtg    360
tatactggct tactatgttg gcactgatga gggtgtcagt gaagtgcttc atgtggcagg    420
agaaaaaagg ctgcaccggt gcgtcagcag aatatgtgat acaggatata ttccgcttcc    480
tcgctcactg actcgctacg ctcggtcgtt cgactgcggc gagcggaaat ggcttacgaa    540
cggggcggag atttcctgga agatgccagg aagatactta acagggaagt gagagggccg    600
cggcaaagcc gtttttccat aggctccgcc cccctgacaa gcatcacgaa atctgacgct    660
caaatcagtg gtggcgaaac ccgacaggac tataaagata ccaggcgttt ccccctggcg    720
gctccctcgt gcgctctcct gttcctgcct ttcggtttac cggtgtcatt ccgctgttat    780
ggccgcgttt gtctcattcc acgcctgaca ctcagttccg ggtaggcagt tcgctccaag    840
ctggactgta tgcacgaacc ccccgttcag tccgaccgct gcgccttatc cggtaactat    900
cgtcttgagt ccaacccgga aagacatgca aaagcaccac tggcagcagc cactggtaat    960
tgatttagag gagttagtct tgaagtcatg cgccggttaa ggctaaactg aaaggacaag   1020
ttttggtgac tgcgctcctc caagccagtt acctcggttc aaagagttgg tagctcagag   1080
aaccttcgaa aaaccgccct gcaaggcggt tttttcgttt tcagagcaag agattacgcg   1140
cagaccaaaa cgatctcaag aagatcatct tattaatcag ataaaatatt tctagatttc   1200
agtgcaattt atctcttcaa atgtagcacc tgaagtcagc cccatacgat ataagttgta   1260
attctcatgt ttgacagctt atcatcgata agcttggtac ccaattatga caacttgacg   1320
gctacatcat tcactttttc ttcacaaccg gcacggaact cgctcgggct ggccccggtg   1380
catttttaa atacccgcga gaaatagagt tgatcgtcaa aaccaacatt gcgaccgacg   1440
gtggcgatag gcatccgggt ggtgctcaaa agcagcttcg cctggctgat acgttggtcc   1500
tcgcgccagc ttaagacgct aatccctaac tgctggcgga aaagatgtga cagacgcgac   1560
ggcgacaagc aaacatgctg tgcgacgctg gcgatatcaa aattgctgtc tgccaggtga   1620
tcgctgatgt actgacaagc ctcgcgtacc cgattatcca tcggtggatg gagcgactcg   1680
ttaatcgctt ccatgcgccg cagtaacaat tgctcaagca gatttatcgc cagcagctcc   1740
gaatagcgcc cttccccttg cccggcgtta atgatttgcc caaacaggtc gctgaaatgc   1800
ggctggtgcg cttcatccgg gcgaaagaac cccgtattgg caaatattga cggccagtta   1860
agccattcat gccagtaggc gcgcggacga aagtaaaccc actggtgata ccattcgcga   1920
gcctccggat gacgaccgta gtgatgaatc tctcctggcg ggaacagcaa aatatcactc   1980
ggtcggcaaa caaattctcg tccctgattt ttcaccaccc cctgaccgcg aatggtgaga   2040
ttgagaatat aacctttcat tcccagcggt cggtcgataa aaaaatcgag ataaccgttg   2100
gcctcaatcg gcgttaaacc cgccaccaga tgggcattaa acgagtatcc cggcagcagg   2160
ggatcatttt gcgcttcagc catacttttc atactcccgc cattcagaga agaaaccaat   2220
tgtccatatt gcatcagaca ttgccgtcac tgcgtctttt actggctctt ctcgctaacc   2280
aaaccggtaa ccccgcttat taaaagcatt ctgtaacaaa gcgggaccaa agccatgaca   2340
aaaacgcgta acaaaagtgt ctataatcac ggcagaaaag tccacattga ttatttgcac   2400
ggcgtcacac tttgctatgc catagcattt ttatccataa gattagcgga tcctacctga   2460
cgctttttat cgcaactctc tactgtttct ccatacccgt ttttttgggc taacaggagg   2520
aattagatct atggacgaat ttgaaatgat aaagagaaac acatctgaaa ttatcagcga   2580
ggaagagtta agagaggttt tagaaaaaga tgaaaagtct gctcttatag gttttgaacc   2640
```

```
aagtggtaaa atacatttag ggcattatct ccaaataaaa aagatgattg atttacaaaa   2700
tgctggattt gatataatta tattgttgtc tgatttaaat gcctatttaa accagaaagg   2760
agagttggat gagattagaa aaatagggga ttataacaaa aaagtttttg aagcaatggg   2820
gttaaaggca aaatatgttt atggaagtga attccagctt gataaggatt atacactgaa   2880
tgtctataga ttggctttaa aaactacctt aaagagagca agaaggagta tggaacttat   2940
agcaagagag gatgaaaatc caaaggttgc tgaagttatc tatccaataa tgcaggttaa   3000
tgatattcat tatttaggcg tcgatgttct ggttggaggg atggagcaga gaaaaataca   3060
catgttagca agggagcttt taccaaaaaa ggttgtttgt attcacaacc ctgtcttaac   3120
gggtttggat ggagaaggaa agatgagttc ttcaaaaggg aattttatag ctgttgatga   3180
ctctccagaa gagattaggg ctaagataaa gaaagcatac tgcccagctg gagttgttga   3240
aggaaatcca ataatggaga tagctaaata cttccttgaa tatcctttaa ccataaaaag   3300
gccagaaaaa tttggtggag atttgacagt taatagctat gaggagttag agagtttatt   3360
taaaaataag gaattgcatc caatggattt aaaaaatgct gtagctgaag aacttataaa   3420
gattttagag ccaattagaa agagattata agtcgaccat catcatcatc atcattgagt   3480
ttaaacggtc tccagcttgg ctgttttggc ggatgagaga agattttcag cctgatacag   3540
attaaatcag aacgcagaag cggtctgata aaacagaatt tgcctggcgg cagtagcgcg   3600
gtggtcccac ctgaccccat gccgaactca gaagtgaaac gccgtagcgc cgatggtagt   3660
gtggggtctc cccatgcgag agtagggaac tgccaggcat caaataaaac gaaaggctca   3720
gtcgaaagac tgggccttgt ttgtgagctc ccggtcatca atcatcccca taatccttgt   3780
tagattatca attttaaaaa actaacagtt gtcagcctgt cccgctttaa tatcatacgc   3840
cgttatacgt tgtttacgct ttgaggaatc ccatatggac gaatttgaaa tgataaagag   3900
aaacacatct gaaattatca gcgaggaaga gttaagagag gttttagaaa aagatgaaaa   3960
gtctgctctt ataggttttg aaccaagtgg taaaatacat ttagggcatt atctccaaat   4020
aaaaaagatg attgatttac aaaatgctgg atttgatata attatattgt tgtctgattt   4080
aaatgcctat ttaaaccaga aaggagagtt ggatgagatt agaaaaatag gggattataa   4140
caaaaaagtt tttgaagcaa tggggttaaa ggcaaaatat gtttatggaa gtgaattcca   4200
gcttgataag gattatacac tgaatgtcta tagattggct ttaaaaacta ccttaaagag   4260
agcaagaagg agtatggaac ttatagcaag agaggatgaa aatccaaagg ttgctgaagt   4320
tatctatcca ataatgcagg ttaatgatat tcattattta ggcgtcgatg ttctggttgg   4380
agggatggag cagagaaaaa tacacatgtt agcaagggag cttttaccaa aaaaggttgt   4440
ttgtattcac aaccctgtct taacgggttt ggatggagaa ggaaagatga gttcttcaaa   4500
agggaatttt atagctgttg atgactctcc agaagagatt agggctaaga taaagaaagc   4560
atactgccca gctggagttg ttgaaggaaa tccaataatg gagatagcta aatacttcct   4620
tgaatatcct ttaaccataa aaaggccaga aaaatttggt ggagatttga cagttaatag   4680
ctatgaggag ttagagagtt tatttaaaaa taaggaattg catccaatgg atttaaaaaa   4740
tgctgtagct gaagaactta taaagatttt agagccaatt agaaagagat tataactgca   4800
gtttcaaacg ctaaattgcc tgatgcgcta cgcttatcag gcctacatga tctctgcaat   4860
atattgagtt tgcgtgcttt tgtaggccgg ataaggcgtt cacgccgcat ccggcaagaa   4920
acagcaaaca atccaaaacg ccgcgttcag cggcgttttt tctgcttttc ttcgcgaatt   4980
```

```
aattccgctt cgcaacatgt gagcaccggt ttattgacta ccggaagcag tgtgaccgtg   5040

tgcttctcaa atgcctgagg ccagtttgct caggctctcc ccgtggaggt aataattgac   5100

gatatgatca gtgcacggct aactaagcgg cctgctgact ttctcgccga tcaaaaggca   5160

ttttgctatt aagggattga cgagggcgta tctgcgcagt aagatgcgcc ccgcattccg   5220

gcggtagttc agcagggcag aacggcggac tctaaatccg catggcaggg gttcaaatcc   5280

cctccgccgg accaaattcg aaaagcctgc tcaacgagca ggctttttttg catgctcgag   5340

cagctcaggg tcgaatttgc tttcgaattt ctgccattca tccgcttatt atcacttatt   5400

caggcgtagc accaggcgtt taagggcacc aataactgcc ttaaaaaaat tacgccccgc   5460

cctgccactc atcgcagtac tgttgtaatt cattaagcat tctgccgaca tggaagccat   5520

cacagacggc atgatgaacc tgaatcgcca gcggcatcag caccttgtcg ccttgcgtat   5580

aatatttgcc catggtgaaa acgggggcga agaagttgtc catattggcc acgtttaaat   5640

caaaactggt gaaactcacc cagggattgg ctgagacgaa aaacatattc tcaataaacc   5700

ctttagggaa ataggccagg ttttcaccgt aacacgccac atcttgcgaa tatatgtgta   5760

gaaactgccg gaaatcgtcg tggtattcac tccagagcga tgaaaacgtt tcagtttgct   5820

catggaaaac ggtgtaacaa gggtgaacac tatcccatat caccagctca ccgtctttca   5880

ttgccatacg gaattccgga tgagcattca tcaggcgggc aagaatgtga ataaaggccg   5940

gataaaactt gtgcttattt ttctttacgg tctttaaaaa ggccgtaata tccagctgaa   6000

cggtctggtt ataggtacat tgagcaactg actgaaatgc ctcaaaatgt tctttacgat   6060

gccattggga tatatcaacg gtggtatatc cagtgatttt tttctccatt ttagcttcct   6120

tagc                                                                6124
```

<210> SEQ ID NO 8
<211> LENGTH: 6124
<212> TYPE: DNA
<213> ORGANISM: Artificial Sequence
<220> FEATURE:
<223> OTHER INFORMATION: Artificial pEvol_DOPA-RS Sequence

<400> SEQUENCE: 8

```
tcctgaaaat ctcgataact caaaaaatac gcccggtagt gatcttattt cattatggtg     60

aaagttggaa cctcttacgt gccgatcaac gtctcatttt cgccaaaagt tggcccaggg    120

cttcccggta tcaacaggga caccaggatt tatttattct gcgaagtgat cttccgtcac    180

aggtatttat tcggcgcaaa gtgcgtcggg tgatgctgcc aacttactga tttagtgtat    240

gatggtgttt ttgaggtgct ccagtggctt ctgtttctat cagctgtccc tcctgttcag    300

ctactgacgg ggtggtgcgt aacggcaaaa gcaccgccgg acatcagcgc tagcggagtg    360

tatactggct tactatgttg gcactgatga gggtgtcagt gaagtgcttc atgtggcagg    420

agaaaaaagg ctgcaccggt gcgtcagcag aatatgtgat acaggatata ttccgcttcc    480

tcgctcactg actcgctacg ctcggtcgtt cgactgcggc gagcggaaat ggcttacgaa    540

cggggcggag atttcctgga agatgccagg aagatactta acagggaagt gagagggccg    600

cggcaaagcc gtttttccat aggctccgcc cccctgacaa gcatcacgaa atctgacgct    660

caaatcagtg gtggcgaaac ccgacaggac tataaagata ccaggcgttt ccccctggcg    720

gctccctcgt gcgctctcct gttcctgcct ttcggtttac cggtgtcatt ccgctgttat    780

ggccgcgttt gtctcattcc acgcctgaca ctcagttccg ggtaggcagt tcgctccaag    840

ctggactgta tgcacgaacc ccccgttcag tccgaccgct gcgccttatc cggtaactat    900
```

```
cgtcttgagt ccaacccgga aagacatgca aaagcaccac tggcagcagc cactggtaat    960
tgatttagag gagttagtct tgaagtcatg cgccggttaa ggctaaactg aaaggacaag   1020
ttttggtgac tgcgctcctc caagccagtt acctcggttc aaagagttgg tagctcagag   1080
aaccttcgaa aaaccgccct gcaaggcggt tttttcgttt tcagagcaag agattacgcg   1140
cagaccaaaa cgatctcaag aagatcatct tattaatcag ataaaatatt tctagatttc   1200
agtgcaattt atctcttcaa atgtagcacc tgaagtcagc cccatacgat ataagttgta   1260
attctcatgt ttgacagctt atcatcgata agcttggtac ccaattatga caacttgacg   1320
gctacatcat tcactttttc ttcacaaccg gcacggaact cgctcgggct ggccccggtg   1380
catttttaa atacccgcga gaaatagagt tgatcgtcaa aaccaacatt gcgaccgacg   1440
gtggcgatag gcatccgggt ggtgctcaaa agcagcttcg cctggctgat acgttggtcc   1500
tcgcgccagc ttaagacgct aatccctaac tgctggcgga aaagatgtga cagacgcgac   1560
ggcgacaagc aaacatgctg tgcgacgctg gcgatatcaa aattgctgtc tgccaggtga   1620
tcgctgatgt actgacaagc ctcgcgtacc cgattatcca tcggtggatg gagcgactcg   1680
ttaatcgctt ccatgcgccg cagtaacaat tgctcaagca gatttatcgc cagcagctcc   1740
gaatagcgcc cttccccttg cccggcgtta atgatttgcc caaacaggtc gctgaaatgc   1800
ggctggtgcg cttcatccgg gcgaaagaac cccgtattgg caaatattga cggccagtta   1860
agccattcat gccagtaggc gcgcggacga aagtaaaccc actggtgata ccattcgcga   1920
gcctccggat gacgaccgta gtgatgaatc tctcctggcg ggaacagcaa aatatcactc   1980
ggtcggcaaa caaattctcg tccctgattt ttcaccaccc cctgaccgcg aatggtgaga   2040
ttgagaatat aacctttcat tcccagcggt cggtcgataa aaaaatcgag ataaccgttg   2100
gcctcaatcg gcgttaaacc cgccaccaga tgggcattaa acgagtatcc cggcagcagg   2160
ggatcatttt gcgcttcagc catacttttc atactcccgc cattcagaga agaaaccaat   2220
tgtccatatt gcatcagaca ttgccgtcac tgcgtctttt actggctctt ctcgctaacc   2280
aaaccggtaa ccccgcttat taaaagcatt ctgtaacaaa gcgggaccaa agccatgaca   2340
aaaacgcgta acaaaagtgt ctataatcac ggcagaaaag tccacattga ttatttgcac   2400
ggcgtcacac tttgctatgc catagcattt ttatccataa gattagcgga tcctacctga   2460
cgctttttat cgcaactctc tactgtttct ccatacccgt ttttttgggc taacaggagg   2520
aattagatct atggacgaat ttgaaatgat aaagagaaac acatctgaaa ttatcagcga   2580
ggaagagtta agagaggttt tagaaaaaga tgaaaagtct gctcttatag gttttgaacc   2640
aagtggtaaa atacatttag ggcattatct ccaaataaaa aagatgattg atttacaaaa   2700
tgctggattt gatataatta tattgttgtc tgatttaaat gcctatttaa accagaaagg   2760
agagttggat gagattagaa aaatagggga ttataacaaa aaagtttttg aagcaatggg   2820
gttaaaggca aaatatgttt atggaagtga attccagctt gataaggatt atacactgaa   2880
tgtctataga ttggctttaa aaactacctt aaagagagca agaaggagta tggaacttat   2940
agcaagagag gatgaaaatc caaaggttgc tgaagttatc tatccaataa tgcaggttaa   3000
tgatattcat tatttaggcg tcgatgttca ggttggaggg atggagcaga gaaaaataca   3060
catgttagca agggagcttt taccaaaaaa ggttgtttgt attcacaacc ctgtcttaac   3120
gggtttggat ggagaaggaa agatgagttc ttcaaaaggg aattttatag ctgttgatga   3180
ctctccagaa gagattaggg ctaagataaa gaaagcatac tgcccagctg gagttgttga   3240
```

-continued

```
aggaaatcca ataatggaga tagctaaata cttccttgaa tatcctttaa ccataaaaag   3300
gccagaaaaa tttggtggag atttgacagt taatagctat gaggagttag agagtttatt   3360
taaaaataag gaattgcatc caatggattt aaaaaatgct gtagctgaag aacttataaa   3420
gattttagag ccaattagaa agagattata agtcgaccat catcatcatc atcattgagt   3480
ttaaacggtc tccagcttgg ctgttttggc ggatgagaga agattttcag cctgatacag   3540
attaaatcag aacgcagaag cggtctgata aaacagaatt tgcctggcgg cagtagcgcg   3600
gtggtcccac ctgaccccat gccgaactca gaagtgaaac gccgtagcgc cgatggtagt   3660
gtggggtctc cccatgcgag agtagggaac tgccaggcat caaataaaac gaaaggctca   3720
gtcgaaagac tgggccttgt ttgtgagctc ccggtcatca atcatcccca taatccttgt   3780
tagattatca attttaaaaa actaacagtt gtcagcctgt cccgctttaa tatcatacgc   3840
cgttatacgt tgtttacgct ttgaggaatc ccatatggac gaatttgaaa tgataaagag   3900
aaacacatct gaaattatca gcgaggaaga gttaagagag gttttagaaa aagatgaaaa   3960
gtctgctctt ataggttttg aaccaagtgg taaaatacat ttagggcatt atctccaaat   4020
aaaaaagatg attgatttac aaaatgctgg atttgatata attatattgt tgtctgattt   4080
aaatgcctat ttaaaccaga aaggagagtt ggatgagatt agaaaaatag ggattataa    4140
caaaaaagtt tttgaagcaa tggggttaaa ggcaaaatat gtttatggaa gtgaattcca   4200
gcttgataag gattatacac tgaatgtcta tagattggct ttaaaaacta ccttaaagag   4260
agcaagaagg agtatggaac ttatagcaag agaggatgaa aatccaaagg ttgctgaagt   4320
tatctatcca ataatgcagg ttaatgatat tcattattta ggcgtcgatg ttcaggttgg   4380
agggatggag cagagaaaaa tacacatgtt agcaagggag cttttaccaa aaaaggttgt   4440
ttgtattcac aaccctgtct taacgggttt ggatggagaa ggaaagatga gttcttcaaa   4500
agggaatttt atagctgttg atgactctcc agaagagatt agggctaaga taaagaaagc   4560
atactgccca gctggagttg ttgaaggaaa tccaataatg gagatagcta aatacttcct   4620
tgaatatcct ttaaccataa aaaggccaga aaaatttggt ggagatttga cagttaatag   4680
ctatgaggag ttagagagtt tatttaaaaa taaggaattg catccaatgg atttaaaaaa   4740
tgctgtagct gaagaactta taaagatttt agagccaatt agaaagagat tataactgca   4800
gtttcaaacg ctaaattgcc tgatgcgcta cgcttatcag gcctacatga tctctgcaat   4860
atattgagtt tgcgtgcttt tgtaggccgg ataaggcgtt cacgccgcat ccggcaagaa   4920
acagcaaaca atccaaaacg ccgcgttcag cggcgttttt tctgcttttc ttcgcgaatt   4980
aattccgctt cgcaacatgt gagcaccggt ttattgacta ccggaagcag tgtgaccgtg   5040
tgcttctcaa atgcctgagg ccagtttgct caggctctcc ccgtggaggt aataattgac   5100
gatatgatca gtgcacggct aactaagcgg cctgctgact ttctcgccga tcaaaaggca   5160
ttttgctatt aagggattga cgagggcgta tctgcgcagt aagatgcgcc ccgcattccg   5220
gcggtagttc agcagggcag aacggcggac tctaaatccg catggcaggg gttcaaatcc   5280
cctccgccgg accaaattcg aaaagcctgc tcaacgagca ggcttttttg catgctcgag   5340
cagctcaggg tcgaatttgc tttcgaattt ctgccattca tccgcttatt atcacttatt   5400
caggcgtagc accaggcgtt taagggcacc aataactgcc ttaaaaaaat tacgccccgc   5460
cctgccactc atcgcagtac tgttgtaatt cattaagcat tctgccgaca tggaagccat   5520
cacagacggc atgatgaacc tgaatcgcca gcggcatcag caccttgtcg ccttgcgtat   5580
aatatttgcc catggtgaaa acgggggcga agaagttgtc catattggcc acgtttaaat   5640
```

```
caaaactggt gaaactcacc cagggattgg ctgagacgaa aaacatattc tcaataaacc   5700

ctttagggaa ataggccagg ttttcaccgt aacacgccac atcttgcgaa tatatgtgta   5760

gaaactgccg gaaatcgtcg tggtattcac tccagagcga tgaaaacgtt tcagtttgct   5820

catggaaaac ggtgtaacaa gggtgaacac tatcccatat caccagctca ccgtctttca   5880

ttgccatacg gaattccgga tgagcattca tcaggcgggc aagaatgtga ataaaggccg   5940

gataaaactt gtgcttattt ttctttacgg tctttaaaaa ggccgtaata tccagctgaa   6000

cggtctggtt ataggtacat tgagcaactg actgaaatgc ctcaaaatgt tctttacgat   6060

gccattggga tatatcaacg gtggtatatc cagtgatttt tttctccatt ttagcttcct   6120

tagc                                                                6124
```

<210> SEQ ID NO 9
<211> LENGTH: 6857
<212> TYPE: DNA
<213> ORGANISM: Artificial Sequence
<220> FEATURE:
<223> OTHER INFORMATION: Artificial pBAD_TPL_Emerald_GFP_E90TAG Sequence

<400> SEQUENCE: 9

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttgggc    300

taacaggagg aattaaccat gagtaaagga gaagaacttt tcactggagt tgtcccaatt    360

cttgttgaat tagatggtga tgttaatggg cacaaatttt ctgtcagtgg agagggtgaa    420

ggtgatgcaa catacggaaa acttaccctt aaatttattt gcactactgg aaaactacct    480

gttccatggc caacacttgt cactactttc acctatggtg ttcaatgctt tgcgcgttat    540

ccggatcaca tgaaacggca tgactttttc aagagtgcca tgccctaggg ttatgtacag    600

gaacgcacta tatctttcaa agatgacggg aactacaaga cgcgtgctga agtcaagttt    660

gaaggtgata cccttgttaa tcgtatcgag ttaaaaggta ttgattttaa agaagatgga    720

aacattctcg gccataagct ggaatataac tacaacagcc acaaggtgta tatcaccgcg    780

gataagcaga agaatggcat caaggccaac ttcaaaaccc gccacaacat tgaagatgga    840

tccgttcaac tagcagacca ttatcaacaa aatactccaa ttggcgatgg ccctgtcctt    900

ttaccagaca accattacct gtcgacacaa tctgcccttt cgaaagatcc caacgaaaag    960

cgtgaccaca tggtccttct tgagtttgta actgctgctg ggattacaca tggcatggat   1020

gagctctaca aactcgagca ccaccaccac caccactgag aattcgaagc ttgggcccga   1080

acaaaaactc atctcagaag aggatctgaa tagcgccgtc gaccatcatc atcatcatca   1140

ttgagtttaa acggtctcca gcttggctgt tttggcggat gagagaagat tttcagcctg   1200

atacagatta aatcagaacg cagaagcggt ctgataaaac agaatttgcc tggcggcagt   1260

agcgcggtgg tcccacctga ccccatgccg aactcagaag tgaaacgccg tagcgccgat   1320

ggtagtgtgg ggtctcccca tgcgagagta gggaactgcc aggcatcaaa taaaacgaaa   1380

ggctcagtcg aaagactggg cctttcgttt tatctgttgt ttgtcggtga acgctctcct   1440

gagtaggaca aatccgccgg gagcggattt gaacgttgcg aagcaacggc ccggagggtg   1500
```

-continued

```
gcgggcagga cgcccgccat aaactgccag gcatcaaatt aagcagaagg ccatcctgac   1560
ggatggcctt tttgcgtttc tacaaactct ttttgtttat ttttctaaat acattcaaat   1620
atgtatccgc tcattgtaca gatctctcct tcacagattc ccaatctctt gttaaataac   1680
gaaaaagcat caatcaaaac ggcggcatgt ctttctatat tccagcaatg ttttataggg   1740
gacatattga tgaagatggg tatcacctta gtaaaaaaag aattgctata agctgctctt   1800
ttttgttcgt gatatactga taataaattg aattttcaca cttctggaaa aaggagatat   1860
accatgaatt atccggcaga acccttccgt attaaaagcg ttgaaactgt atctatgatc   1920
ccgcgtgatg aacgcctcaa gaaaatgcag gaagcgggtt acaatacttt cctgttaaat   1980
tcgaaagata tttatattga cctgctgaca gacagtggca ctaacgcaat gagcgacaag   2040
cagtgggccg gaatgatgat gggtgatgaa gcgtacgcgg gcagcgaaaa cttctatcat   2100
ctggaaagaa ccgtgcagga actgttcggc tttaaacata ttgttccgac tcaccagggg   2160
cgtggcgcag aaaacctgtt atcgcagttg gctattaaac ctgggcaata tgttgccggg   2220
aatatgtatt tcaccaccac ccgttatcac caggaaaaaa atggtgcggt gtttgtcgat   2280
atcgttcgtg acgaagcgca cgatgccggt ctgaatattg cgtttaaagg tgatatcgat   2340
cttaaaaaat tacaaaagct gattgatgaa aaaggcgcag aaaatattgc gtatatctgc   2400
ctggcggtga cggttaacct cgcaggtggg cagccggtct cgatggccaa catgcgtgcg   2460
gtgcgtgaac tgacagaagc gcacggcatt aaagtgttct acgacgccac ccgttgcgtg   2520
gaaaacgcct actttatcaa agagcaagag cagggctttg agaacaagag catcgccgag   2580
atcgtgcatg agatgttcag ctacgccgac ggttgtacca tgagtggtaa aaaagactgt   2640
ctggtgaaca tcggcggttt cctgtgcatg aacgatgacg aaatgttctc ttctgccaaa   2700
gagttagtcg tggtctacga agggatgcca tcttacggcg gcctggccgg acgtgatatg   2760
gaagccatgg cgattggcct gcgcgaagcc atgcaatacg aatatattga gcaccgcgtg   2820
aagcaggttc gctacctggg cgataagctg aaagccgctg gcgtaccgat tgttgaaccg   2880
gtaggcggtc acgcggtatt cctcgatgcg cgtcgcttct gcgagcatct gacgcaggac   2940
gagttcccgg cgcaaagcct ggcggcgagc atttatgtgg aaactggtgt gcgcagtatg   3000
gaacgcggaa taatctctgc aggccgtaat aacgtgaccg gtgaacacca cagaccgaaa   3060
ctggaaaccg tgcgtctgac tattccacgc cgcgtttata cctacgcgca catggatgtc   3120
gtagctgacg gtattattaa actttaccag cacaaagaag atattcgcgg gctgaagttt   3180
atttacgagc cgaagcagtt gcgtttcttt actgcacgct ttgactatat ccatcaccat   3240
catcaccatt aactgcaggc atgcaagctt ggctgttttg gcggatgaga gaagattttc   3300
agcctgatac agattaaatc agaacgcaga agcggtctga taaaacagaa tttgcctggc   3360
ggcagtagcg cggtggtccc acctgacccc atgccgaact cagaagtgaa acgccgtagc   3420
gccgatggta gtgtggggtc tccccatgcg agagtaggga actgccaggc atcaaataaa   3480
acgaaaggct cagtcgaaag actgggcctt tcgttttatc tgttgtttgt cggtgaacgc   3540
tctcctgagt aggacaaatc cgccgggagc ggatttgaac gttgcgaagc aacggcccgg   3600
agggtggcgg gcaggacgcc cgccataaac tgccaggcat caaattaagc agaaggccat   3660
cctgacggat ggcctttttg cgtttctaca aacttgtaca ataaccctga taaatgcttc   3720
aataatattg aaaaaggaag agtatgagta ttcaacattt ccgtgtcgcc cttattccct   3780
tttttgcggc attttgcctt cctgtttttg ctcacccaga aacgctggtg aaagtaaaag   3840
atgctgaaga tcagttgggt gcacgagtgg gttacatcga actggatctc aacagcggta   3900
```

```
agatccttga gagttttcgc cccgaagaac gttttccaat gatgagcact tttaaagttc   3960
tgctatgtgg cgcggtatta tcccgtgttg acgccgggca agagcaactc ggtcgccgca   4020
tacactattc tcagaatgac ttggttgagt actcaccagt cacagaaaag catcttacgg   4080
atggcatgac agtaagagaa ttatgcagtg ctgccataac catgagtgat aacactgcgg   4140
ccaacttact tctgacaacg atcggaggac cgaaggagct aaccgctttt ttgcacaaca   4200
tgggggatca tgtaactcgc cttgatcgtt gggaaccgga gctgaatgaa gccataccaa   4260
acgacgagcg tgacaccacg atgcctgtag caatggcaac aacgttgcgc aaactattaa   4320
ctggcgaact acttactcta gcttcccggc aacaattaat agactggatg gaggcggata   4380
aagttgcagg accacttctg cgctcggccc ttccggctgg ctggtttatt gctgataaat   4440
ctggagccgg tgagcgtggg tctcgcggta tcattgcagc actggggcca gatggtaagc   4500
cctcccgtat cgtagttatc tacacgacgg ggagtcaggc aactatggat gaacgaaata   4560
gacagatcgc tgagataggt gcctcactga ttaagcattg gtaactgtca gaccaagttt   4620
actcatatat actttagatt gatttaaaac ttcattttta atttaaaagg atctaggtga   4680
agatcctttt tgataatctc atgaccaaaa tcccttaacg tgagttttcg ttccactgag   4740
cgtcagaccc cgtagaaaag atcaaaggat cttcttgaga tccttttttt ctgcgcgtaa   4800
tctgctgctt gcaaacaaaa aaaccaccgc taccagcggt ggtttgtttg ccggatcaag   4860
agctaccaac tctttttccg aaggtaactg gcttcagcag agcgcagata ccaaatactg   4920
tccttctagt gtagccgtag ttaggccacc acttcaagaa ctctgtagca ccgcctacat   4980
acctcgctct gctaatcctg ttaccagtgg ctgctgccag tggcgataag tcgtgtctta   5040
ccgggttgga ctcaagacga tagttaccgg ataaggcgca gcggtcgggc tgaacggggg   5100
gttcgtgcac acagcccagc ttggagcgaa cgacctacac cgaactgaga tacctacagc   5160
gtgagctatg agaaagcgcc acgcttcccg aagggagaaa ggcggacagg tatccggtaa   5220
gcggcagggt cggaacagga gagcgcacga gggagcttcc agggggaaac gcctggtatc   5280
tttatagtcc tgtcgggttt cgccacctct gacttgagcg tcgatttttg tgatgctcgt   5340
caggggggcg gagcctatgg aaaaacgcca gcaacgcggc ctttttacgg ttcctggcct   5400
tttgctggcc ttttgctcac atgttctttc ctgcgttatc ccctgattct gtggataacc   5460
gtattaccgc ctttgagtga gctgataccg ctcgccgcag ccgaacgacc gagcgcagcg   5520
agtcagtgag cgaggaagcg gaagagcgcc tgatgcggta ttttctcctt acgcatctgt   5580
gcggtatttc acaccgcata tggtgcactc tcagtacaat ctgctctgat gccgcatagt   5640
taagccagta tacactccgc tatcgctacg tgactgggtc atggctgcgc cccgacaccc   5700
gccaacaccc gctgacgcgc cctgacgggc ttgtctgctc ccggcatccg cttacagaca   5760
agctgtgacc gtctccggga gctgcatgtg tcagaggttt tcaccgtcat caccgaaacg   5820
cgcgaggcag cagatcaatt cgcgcgcgaa ggcgaagcgg catgcataat gtgcctgtca   5880
aatggacgaa gcagggattc tgcaaaccct atgctactcc gtcaagccgt caattgtctg   5940
attcgttacc aattatgaca acttgacggc tacatcattc actttttctt cacaaccggc   6000
acggaactcg ctcgggctgg ccccggtgca tttttaaat acccgcgaga aatagagttg   6060
atcgtcaaaa ccaacattgc gaccgacggt ggcgataggc atccgggtgg tgctcaaaag   6120
cagcttcgcc tggctgatac gttggtcctc gcgccagctt aagacgctaa tccctaactg   6180
ctggcggaaa agatgtgaca gacgcgacgg cgacaagcaa acatgctgtg cgacgctggc   6240
```

```
gatatcaaaa ttgctgtctg ccaggtgatc gctgatgtac tgacaagcct cgcgtacccg   6300

attatccatc ggtggatgga gcgactcgtt aatcgcttcc atgcgccgca gtaacaattg   6360

ctcaagcaga tttatcgcca gcagctccga atagcgccct tccccttgcc cggcgttaat   6420

gatttgccca aacaggtcgc tgaaatgcgg ctggtgcgct tcatccgggc gaaagaaccc   6480

cgtattggca aatattgacg gccagttaag ccattcatgc cagtaggcgc gcggacgaaa   6540

gtaaacccac tggtgatacc attcgcgagc ctccggatga cgaccgtagt gatgaatctc   6600

tcctggcggg aacagcaaaa tatcacccgg tcggcaaaca aattctcgtc cctgattttt   6660

caccaccccc tgaccgcgaa tggtgagatt gagaatataa cctttcattc ccagcggtcg   6720

gtcgataaaa aaatcgagat aaccgttggc ctcaatcggc gttaaacccg ccaccagatg   6780

ggcattaaac gagtatcccg gcagcagggg atcattttgc gcttcagcca tacttttcat   6840

actcccgcca ttcagag                                                  6857
```

```
<210> SEQ ID NO 10
<211> LENGTH: 4809
<212> TYPE: DNA
<213> ORGANISM: Artificial Sequence
<220> FEATURE:
<223> OTHER INFORMATION: Artificial pBAD_Emerald_GFP_E90TAG Sequence

<400> SEQUENCE: 10

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttgggc     300

taacaggagg aattaaccat gagtaaagga gaagaacttt tcactggagt tgtcccaatt    360

cttgttgaat tagatggtga tgttaatggg cacaaatttt ctgtcagtgg agagggtgaa    420

ggtgatgcaa catacggaaa acttaccctt aaatttattt gcactactgg aaaactacct    480

gttccatggc caacacttgt cactactttc acctatggtg ttcaatgctt tgcgcgttat    540

ccggatcaca tgaaacggca tgactttttc aagagtgcca tgccctaggg ttatgtacag    600

gaacgcacta tatctttcaa agatgacggg aactacaaga cgcgtgctga agtcaagttt    660

gaaggtgata cccttgttaa tcgtatcgag ttaaaaggta ttgattttaa agaagatgga    720

aacattctcg gccataagct ggaatataac tacaacagcc acaaggtgta tatcaccgcg    780

gataagcaga agaatggcat caaggccaac ttcaaaaccc gccacaacat tgaagatgga    840

tccgttcaac tagcagacca ttatcaacaa aatactccaa ttggcgatgg ccctgtcctt    900

ttaccagaca accattacct gtcgacacaa tctgcccttt cgaaagatcc caacgaaaag    960

cgtgaccaca tggtccttct tgagtttgta actgctgctg ggattacaca tggcatggat   1020

gagctctaca aactcgagca ccaccaccac caccactgag gtaccatatg ggaattcgaa   1080

gcttgggccc gaacaaaaac tcatctcaga agaggatctg aatagcgccg tcgaccatca   1140

tcatcatcat cattgagttt aaacggtctc cagcttggct gttttggcgg atgagagaag   1200

attttcagcc tgatacagat taaatcagaa cgcagaagcg gtctgataaa acagaatttg   1260

cctggcggca gtagcgcggt ggtcccacct gaccccatgc cgaactcaga agtgaaacgc   1320

cgtagcgccg atggtagtgt ggggtctccc catgcgagag tagggaactg ccaggcatca   1380

aataaaacga aaggctcagt cgaaagactg ggcctttcgt tttatctgtt gtttgtcggt   1440
```

```
gaacgctctc ctgagtagga caaatccgcc gggagcggat ttgaacgttg cgaagcaacg   1500
gcccggaggg tggcgggcag gacgcccgcc ataaactgcc aggcatcaaa ttaagcagaa   1560
ggccatcctg acggatggcc tttttgcgtt tctacaaact ctttttgttt atttttctaa   1620
atacattcaa atatgtatcc gctcatgaga caataaccct gataaatgct tcaataatat   1680
tgaaaaagga agagtatgag tattcaacat ttccgtgtcg cccttattcc cttttttgcg   1740
gcattttgcc ttcctgtttt tgctcaccca gaaacgctgg tgaaagtaaa agatgctgaa   1800
gatcagttgg gtgcacgagt gggttacatc gaactggatc tcaacagcgg taagatcctt   1860
gagagttttc gccccgaaga acgttttcca atgatgagca cttttaaagt tctgctatgt   1920
ggcgcggtat tatcccgtgt tgacgccggg caagagcaac tcggtcgccg catacactat   1980
tctcagaatg acttggttga gtactcacca gtcacagaaa agcatcttac ggatggcatg   2040
acagtaagag aattatgcag tgctgccata accatgagtg ataacactgc ggccaactta   2100
cttctgacaa cgatcggagg accgaaggag ctaaccgctt ttttgcacaa catgggggat   2160
catgtaactc gccttgatcg ttgggaaccg gagctgaatg aagccatacc aaacgacgag   2220
cgtgacacca cgatgcctgt agcaatggca acaacgttgc gcaaactatt aactggcgaa   2280
ctacttactc tagcttcccg gcaacaatta atagactgga tggaggcgga taaagttgca   2340
ggaccacttc tgcgctcggc ccttccggct ggctggttta ttgctgataa atctggagcc   2400
ggtgagcgtg ggtctcgcgg tatcattgca gcactggggc cagatggtaa gccctcccgt   2460
atcgtagtta tctacacgac ggggagtcag gcaactatgg atgaacgaaa tagacagatc   2520
gctgagatag gtgcctcact gattaagcat tggtaactgt cagaccaagt ttactcatat   2580
atactttaga ttgatttaaa acttcatttt taatttaaaa ggatctaggt gaagatcctt   2640
tttgataatc tcatgaccaa aatcccttaa cgtgagtttt cgttccactg agcgtcagac   2700
cccgtagaaa agatcaaagg atcttcttga gatccttttt ttctgcgcgt aatctgctgc   2760
ttgcaaacaa aaaaaccacc gctaccagcg gtggtttgtt tgccggatca agagctacca   2820
actctttttc cgaaggtaac tggcttcagc agagcgcaga taccaaatac tgtccttcta   2880
gtgtagccgt agttaggcca ccacttcaag aactctgtag caccgcctac atacctcgct   2940
ctgctaatcc tgttaccagt ggctgctgcc agtggcgata agtcgtgtct taccgggttg   3000
gactcaagac gatagttacc ggataaggcg cagcggtcgg gctgaacggg gggttcgtgc   3060
acacagccca gcttggagcg aacgacctac accgaactga gatacctaca gcgtgagcta   3120
tgagaaagcg ccacgcttcc cgaagggaga aaggcggaca ggtatccggt aagcggcagg   3180
gtcggaacag gagagcgcac gagggagctt ccagggggaa acgcctggta tctttatagt   3240
cctgtcgggt ttcgccacct ctgacttgag cgtcgatttt tgtgatgctc gtcagggggg   3300
cggagcctat ggaaaaacgc cagcaacgcg gcctttttac ggttcctggc cttttgctgg   3360
ccttttgctc acatgttctt tcctgcgtta tcccctgatt ctgtggataa ccgtattacc   3420
gcctttgagt gagctgatac cgctcgccgc agccgaacga ccgagcgcag cgagtcagtg   3480
agcgaggaag cggaagagcg cctgatgcgg tattttctcc ttacgcatct gtgcggtatt   3540
tcacaccgca tatggtgcac tctcagtaca atctgctctg atgccgcata gttaagccag   3600
tatacactcc gctatcgcta cgtgactggg tcatggctgc gccccgacac ccgccaacac   3660
ccgctgacgc gccctgacgg gcttgtctgc tcccggcatc cgcttacaga caagctgtga   3720
ccgtctccgg gagctgcatg tgtcagaggt tttcaccgtc atcaccgaaa cgcgcgaggc   3780
```

-continued

```
agcagatcaa ttcgcgcgcg aaggcgaagc ggcatgcata atgtgcctgt caaatggacg   3840

aagcagggat tctgcaaacc ctatgctact ccgtcaagcc gtcaattgtc tgattcgtta   3900

ccaattatga caacttgacg gctacatcat tcactttttc ttcacaaccg gcacggaact   3960

cgctcgggct ggccccggtg catttttaa atacccgcga gaaatagagt tgatcgtcaa   4020

aaccaacatt gcgaccgacg gtggcgatag gcatccgggt ggtgctcaaa agcagcttcg   4080

cctggctgat acgttggtcc tcgcgccagc ttaagacgct aatccctaac tgctggcgga   4140

aaagatgtga cagacgcgac ggcgacaagc aaacatgctg tgcgacgctg gcgatatcaa   4200

aattgctgtc tgccaggtga tcgctgatgt actgacaagc ctcgcgtacc cgattatcca   4260

tcggtggatg gagcgactcg ttaatcgctt ccatgcgccg cagtaacaat tgctcaagca   4320

gatttatcgc cagcagctcc gaatagcgcc cttccccttg cccggcgtta atgatttgcc   4380

caaacaggtc gctgaaatgc ggctggtgcg cttcatccgg gcgaaagaac cccgtattgg   4440

caaatattga cggccagtta agccattcat gccagtaggc gcgcggacga aagtaaaccc   4500

actggtgata ccattcgcga gcctccggat gacgaccgta gtgatgaatc tctcctggcg   4560

ggaacagcaa aatatcaccc ggtcggcaaa caaattctcg tccctgattt ttcaccaccc   4620

cctgaccgcg aatggtgaga ttgagaatat aacctttcat tcccagcggt cggtcgataa   4680

aaaaatcgag ataaccgttg gcctcaatcg gcgttaaacc cgccaccaga tgggcattaa   4740

acgagtatcc cggcagcagg ggatcatttt gcgcttcagc catacttttc atactcccgc   4800

cattcagag                                                           4809


<210> SEQ ID NO 11
<211> LENGTH: 11
<212> TYPE: PRT
<213> ORGANISM: Artificial sequence
<220> FEATURE:
<223> OTHER INFORMATION: Peptide E sequence

<400> SEQUENCE: 11

Ser Ala Met Pro Glu Gly Tyr Val Gln Glu Arg
1               5                   10
```

INTRODUCING METHOD OF L-DIHYDROXYPHENYLALANINE IN TARGET PROTEIN

CROSS-REFERENCE TO RELATED APPLICATION

This application claims the benefit under 35 USC 119(a) of Korean Patent Application No. 10-2017-0088940 filed on Jul. 13, 2017 in the Korean Intellectual Property Office, the entire disclosure of which is incorporated herein by reference for all purposes.

TECHNICAL FIELD

The present disclosure relates to a method of genetically incorporating an L-dihydroxyphenylalanine (DOPA) in a target protein, and a method of conjugating a protein in which L-dihydroxyphenylalanine is genetically incorporated.

BACKGROUND

L-dihydroxyphenylalanine (L-DOPA) is an amino acid having interesting biochemical properties and found in the biosynthesis of catecholamines in animals and plants. The amino acids have been used for the treatment of Parkinson's disease and various biochemical applications and is produced from tyrosine by tyrosine hydroxylase and molecular oxygen ($O_2$). L-DOPA is a precursor of dopamine and can across the blood-brain barrier (BBB), and thus has been used for the treatment of Parkinson's disease. L-DOPA is also found in mussel adhesion proteins (MAP) contributing to the wet adhesion of mussels. Although it is known that tyrosine is encoded at a site of mussel adhesion protein from which L-DOPA is found and then converted into L-DOPA by tyrosinase, the adhesion of mussels is mainly derived from L-DOPA.

Because of its interesting biochemical properties, L-DOPA has been used in various ways. A dihydroxy group in L-DOPA can be easily oxidized and easily converted into L-dopaquinone as a precursor of melanin. Due to high electrophilicity, L-dopaquinone and its derivatives have been used for cross-linking and conjugation of thiol and amine. 1,2-quinone can also act as diene for cycloaddition reaction and has been used for bioconjugation by SPOCQ (strain-promoted oxidation-controlled cyclooctyne-1,2-quinone) cycloaddition reaction. Further, the dihydroxy group can chelate metal ions such as $Fe^{3+}$ and $Cu^{2+}$, and a protein containing L-DOPA has been used for drug delivery and metal ion sensing.

Japanese Patent Laid-open Publication No. 2012-538313 discloses a novel viral vector construct for neuron specific optimized continuous DOPA synthesis in vivo.

SUMMARY

In view of the foregoing, the present disclosure provides a method of genetically incorporating an L-dihydroxyphenylalanine in a target protein, and a method of conjugating a protein in which L-dihydroxyphenylalanine is genetically incorporated.

However, problems to be solved by the present disclosure are not limited to the above-described problem. Although not described herein, other problems to be solved by the present disclosure can be clearly understood by those skilled in the art from the following descriptions.

In accordance with an aspect of the present disclosure, there is provided a method of genetically incorporating an L-dihydroxyphenylalanine in a target protein, including: genetically incorporating an expression vector including a gene of SEQ ID NO: 1 or SEQ ID NO: 2 into a prokaryote to obtain a transformant; culturing the transformant in a medium so that the prokaryote biosynthesizes L-dihydroxyphenylalanine (L-DOPA) and the biosynthesized L-dihydroxyphenylalanine is incorporated into a target protein contained in the prokaryote; and separating or purifying the L-dihydroxyphenylalanine-incorporated the target protein from the prokaryote.

In accordance with another aspect of the present disclosure, there is provided a method of protein conjugation, including conjugating a protein in which L-DOPA is genetically incorporated with a drug or phosphor by using a strain-promoted oxidation-controlled cyclooctyne-1,2-quinone (SPOCQ) cycloaddition reaction.

In accordance with an embodiment of the present disclosure, L-dihydroxyphenylalanine (L-DOPA) can be biosynthesized from starting materials including catechol, pyruvate, and ammonia by using a tyrosine phenol-lyase (TPL) and the biosynthesized L-DOPA can be directly incorporated into proteins by the genetic incorporation using a pair of a novel aminoacyl-tRNA synthetase (aaRS) and aminoacyl-tRNA.

The novel aminoacyl-tRNA synthetase, i.e., DOPA-RS1 or DOPA-RS2, according to an embodiment of the present disclosure can show better efficiency than the previously reported aminoacyl-tRNA synthetase. Therefore, the incorporation method of L-DOPA according to an embodiment of the present disclosure can mass-produce mutant proteins containing L-DOPA without incorporating tyrosine at lower cost (less than 10%) and higher yield (greater than about 200%) for pharmaceutical and industrial applications than a conventional genetic incorporation system using DOPA-RS without using a tyrosine phenol-lyase (TPL).

In accordance with an embodiment of the present disclosure, a strain-promoted oxidation controlled cyclooctyne-1,2-quinone (SPOCQ) cycloaddition reaction can be used to selectively conjugate a protein in which L-DOPA is genetically incorporated with a drug or phosphor to the L-DOPA site incorporated into the protein.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 1A is a graph showing fluorescence measured from emGFP mutants expressed by three aaRS mutants for L-DOPA incorporated into position 39 of emGFP. FIG. 1B is a graph showing fluorescence measured from emGFP mutants expressed by three aaRS mutants for L-DOPA incorporated into position 90 of emGFP.

In FIG. 2, peptide E (residue 86-96; SAMPEGYVQER) is a tryptic peptide fragment containing 90 residues generated by trypsin digestion, and peptide Y and peptide DOPA contain tyrosine and L-DOPA at position 90.

In FIG. 4, the emGFP gene containing TAG codon at position 90 was expressed by the system illustrated in FIG. 3.

In FIG. 5, peptide E (residue 86-96; SAMPEGYVQER) is a tryptic peptide fragment containing 90 residues generated by trypsin digestion, and peptide Y and peptide DOPA contain tyrosine and L-DOPA at position 90.

FIG. 6A compares general genetic incorporation of L-DOPA with direct incorporation of L-DOPA biosynthesized from TPL. FIG. 6B compares emGFP fluorescence between general genetic incorporation of L-DOPA and direct incorporation of L-DOPA biosynthesized from TPL. FIG. 6C compares cell density between general genetic incorporation of L-DOPA and direct incorporation of L-DOPA biosynthesized from TPL.

FIG. 7A shows the result of SDS-PAGE of MBP-K313DOPA and ADIBOCy5.5. FIG. 7B is a graph showing the result of MALDI-TOF MS analysis of MBP-K313DOPA and ADIBOCy5.5.

DETAILED DESCRIPTION

Figure 1A:
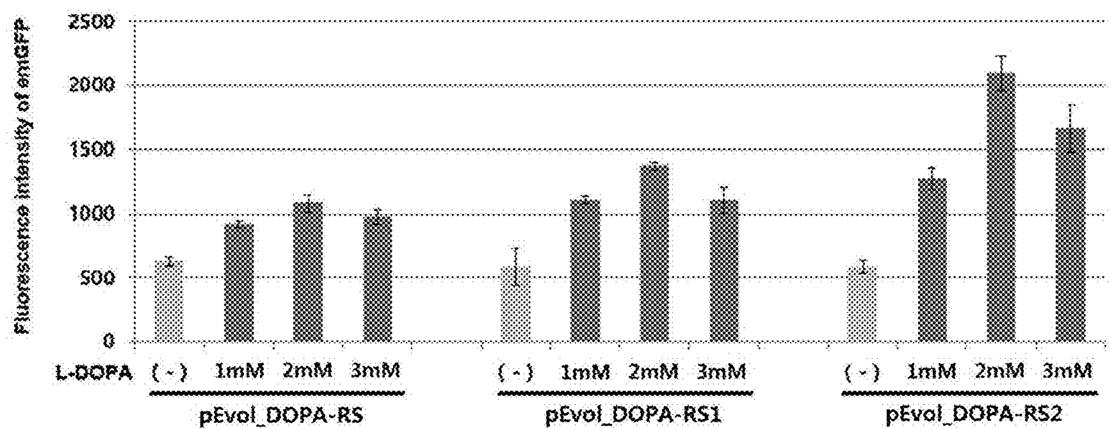
FIGS. 1A and 1B provide graphs showing fluorescence measured from emGFP mutants expressed by three aaRS mutants (Comparative Example 1: DOPA-RS, Example 1: DOPA-RS1, Example: DOPA-RS2) in an example of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for simplicity of explanation, and like reference numerals denote like parts through the whole document.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically or electrostatically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "expression vector" or "vector" refers to a means for incorporating a nucleic acid sequence encoding a target protein into a host cell. In an embodiment of the present disclosure, the expression vector or vector may include a member selected from the group consisting of a plasmid vector, a cosmid vector, a viral vector, and combinations thereof. A suitable expression vector includes expression regulatory elements, such as a promoter, an operator, an initiation codon, a termination codon, a polyadenylation signal or an enhancer, and a signal sequence or leader sequence for membrane targeting or secretion, and may be prepared in various constructs according to the intended use. The initiation codon and the termination codon are generally considered as a part of a nucleotide sequence encoding a target protein, and need to have actions in a subject when a gene construct is administered and be in frame with a coding sequence. A promoter of the expression vector or vector may be constitutive or inducible. Further, the expression vector or vector includes a selective marker for selecting host cells containing the vector, and in the case where the expression vector or vector is a replicable expression vector, the vector may include a replication origin. The expression vector or vector can be self-replicated or integrated into host genomic DNA.

Hereinafter, embodiments and examples of the present disclosure will be described in detail with reference to the accompanying drawings. However, the present disclosure may not be limited to the following embodiments and examples.

In accordance with a first aspect of the present disclosure, there is provided a method of genetically incorporating an L-dihydroxyphenylalanine in a target protein, including: genetically incorporating an expression vector including a gene of SEQ ID NO: 1 or SEQ ID NO: 2 into a prokaryote to obtain a transformant; culturing the transformant in a medium so that the prokaryote biosynthesizes L-dihydroxyphenylalanine (L-DOPA) and the biosynthesized L-dihydroxyphenylalanine is incorporated into a target protein contained in the prokaryote; and separating or purifying the L-dihydroxyphenylalanine-incorporated target protein from the prokaryote.

In an embodiment of the present disclosure, the SEQ ID NO: 1 may represent a gene of a novel aminoacyl-tRNA synthetase 1 (referred to as "DOPA-RS1" through the whole document), and the DOPA-RS1 may be represented by SEQ ID NO: 3.

In an embodiment of the present disclosure, the SEQ ID NO: 2 may represent a gene of a novel aminoacyl-tRNA synthetase 2 (referred to as "DOPA-RS2" through the whole document), and the DOPA-RS2 may be represented by SEQ ID NO: 4.

In an embodiment of the present disclosure, the incorporation of the L-dihydroxyphenylalanine into the target protein may be performed by using a pair of DOPA-RS1 or DOPA-RS2 as a novel aminoacyl-tRNA synthetase (assRS) of SEQ ID NO: 3 or SEQ ID NO: 4 with an aminoacyl-tRNA (aa-tRNA) of SEQ ID NO: 5.

In an embodiment of the present disclosure, the expression vector including a gene of SEQ ID NO: 1 or SEQ ID NO: 2 may be transformed into a prokaryote to prepare a transformant.

In an embodiment of the present disclosure, the expression vector may include a member selected from the group consisting of pEvol, pBK, pHCE, pSub, pT7, pET/Rb, pGEX, pET28a, pET-22b(+), and combinations thereof, but may not be limited thereto.

In an embodiment of the present disclosure, the transformation may refer to co-transformation of the expression vector including a gene of SEQ ID NO: 1 or SEQ ID NO: 2 with an expression vector including a gene encoding tyrosine phenol-lyase (TPL) and emerald green fluorescent protein (emGFP) into the prokaryote.

In an embodiment of the present disclosure, the prokaryote into the expression vector including a gene of SEQ ID NO: 1 or SEQ ID NO: 2 can be easily transformed by using a typical method. For example, the transformation may be performed by heat shock, calcium phosphate method, calcium chloride/rubidium chloride method, electroporation, eletroinjection, chemical processing method, or gene gun, but may not be limited thereto.

In an embodiment of the present disclosure, the L-DOPA-incorporated target protein is a protein included in the prokaryote and may not be limited to a specific sequence.

In an embodiment of the present disclosure, the prokaryote as the co-transformed transformant may be cultured in a medium.

In an embodiment of the present disclosure, the prokaryote serves as a host cell in which an expression vector is incorporated and may use any prokaryote which can express its target gene or protein. For example, the prokaryotes may include a member selected from the group consisting of *Escherichia* genus, *Serratia* genus, *Corynebacterium* genus, *Brevibacterium* genus, *Pseudomonas* genus, *Bacillus* genus, *Microbacterium* genus, and combinations thereof, but may not be limited thereto. For example, the *Escherichia coli* strain may include a member selected from the group consisting of DH10B, XL1-Blue, Top10, BL21(DE3), DH5α, and combinations thereof, but may not be limited thereto.

In an embodiment of the present disclosure, the medium may include catechol, pyruvate, and ammonia. For example, the co-transformed transformant may be amplified in the medium including catechol, pyruvate, and ammonia, and may biosynthesize the L-DOPA from the catechol, pyruvate, and ammonia as starting materials by using the TPL, but may not be limited thereto.

In an embodiment of the present disclosure, culture conditions for the transformant may vary depending on a host cell. When the transformant is cultured, temperature, pH of the medium, or culture time can be appropriately adjusted to be suitable for the growth and development of a host cell and the mass production of a target protein. For example, the transformant, i.e., transformed prokaryote may be cultured in the medium at about 10° C. to about 50° C., but may not be limited thereto.

In an embodiment of the present disclosure, the biosynthesized L-DOPA may have a concentration of about 3 mM or more, for example, from about 3 mM to about 4 mM, from about 3 mM to about 3.5 mM, or from about 3.5 mM to about 4 mM, but may not be limited thereto.

In an embodiment of the present disclosure, if the biosynthesized L-DOPA has a concentration of less than about 3 mM, the selectivity is decreased due to competition caused by structural similarity between tyrosine and L-DOPA, which may cause a decrease in incorporation rate of L-DOPA, and if the biosynthesized L-DOPA has a concentration of more than about 4 mM, the L-DOPA is converted into toxic L-dopaquinone and the toxicity may be increased, which may adversely affect protein expression. Therefore, the biosynthesized L-DOPA may have a concentration of about 3 mM or more and desirably from about 3 mM to about 4 mM.

In an embodiment of the present disclosure, the target protein may include a member selected from the group consisting of a green fluorescent protein (GFP), an emerald green fluorescent protein (emGFP), an enhanced green fluorescent protein (eGFP), a maltose-binding protein (MBP), and combinations thereof, but may not be limited thereto.

In an embodiment of the present disclosure, the catechol in the medium may have a concentration of from about 1 mM to about 10 mM, but may not be limited thereto. For example, the catechol in the medium may have a concentration of from about 1 mM to about 10 mM, from about 1 mM to about 8 mM, from about 1 mM to about 6 mM, from about 1 mM to about 4 mM, from about 1 mM to about 2 mM, from about 2 mM to about 10 mM, from about 2 mM to about 8 mM, from about 2 mM to about 6 mM, from about 2 mM to about 4 mM, from about 4 mM to about 10 mM, from about 4 mM to about 8 mM, from about 4 mM to about 6 mM, from about 6 mM to about 10 mM, from about 6 mM to about 8 mM, from about 8 mM to about 10 mM, or from about 5 mM to about 10 mM and specifically from about 6 mM to about 8 mM, but may not be limited thereto.

In an embodiment of the present disclosure, as the concentration of the catechol in the medium increases, the concentration of the biosynthesized and incorporated L-DOPA may increase, but may not be limited thereto.

In an embodiment of the present disclosure, if the catechol in the medium has a concentration of less than about 1 mM, the incorporation rate of L-DOPA into a protein may be decreased due to structural similarity between tyrosine and L-DOPA, and if the catechol has a concentration of more than about 10 mM, toxicity can be observed. Therefore, desirably, the catechol in the medium may have a concentration of from about 1 mM to about 10 mM.

In an embodiment of the present disclosure, the separating or purifying of the target protein may be performed by using electrophoresis, centrifugation, gel permeation, precipitation, dialysis, or chromatography, but may not be limited thereto. For example, the chromatography may include ion-exchange chromatography, affinity chromatography, immunosorbent affinity chromatography, reversed phase HPLC (reversed phase high speed liquid chromatography, reversed phase high performance liquid chromatography), or gel permeation HPLC, but may not be limited thereto.

In an embodiment of the present disclosure, a mutant protein produced from the transformant may be separated or purified by lysing collected procells with an ultrasonicator and then performing column chromatography to a water-soluble fraction of the lysed cells. The purified protein may be produced in the form of powder by removing components remaining in a protein aqueous solution except water and protein through dialysis and then lyophilization, but may not be limited thereto.

In accordance with a second aspect of the present disclosure, there is provided a method of protein conjugation, including conjugating a protein in which L-DOPA is genetically incorporated with a drug or phosphor by using a strain-promoted oxidation-controlled cyclooctyne-1,2-quinone (SPOCQ) cycloaddition reaction.

Detailed descriptions of the second aspect of the present disclosure, which overlap with those of the first aspect of the present disclosure, are omitted hereinafter, but the descriptions of the first aspect of the present disclosure may be identically applied to the second aspect of the present disclosure, even though they are omitted hereinafter.

In an embodiment of the present disclosure, the drug or phosphor is selectively conjugated to the L-DOPA site incorporated into the protein.

In an embodiment of the present disclosure, the protein in which the L-DOPA is genetically incorporated may be produced by the method of the first aspect of the present disclosure.

In an embodiment of the present disclosure, the drug may include a member selected from the group consisting of an anticancer drug, a hormone, an antibiotic, a painkiller, an anti-infective, an antiviral drug, an anti-inflammatory drug, a protein or peptide drug, a nucleic acid, and combinations thereof, but may not be limited thereto.

In an embodiment of the present disclosure, the protein may include a member selected from the group consisting of a hormone, a cytokine, an enzyme, an antibody, a growth factor, a transcriptional regulatory factor, a blood factor, a vaccine, a structural protein, a ligand protein and receptor, a cell surface antigen, a receptor antagonist, and combinations thereof, but may not be limited thereto.

Hereinafter, the present disclosure will be explained in more detail with reference to Examples. However, the following Examples are illustrative only for better understanding of the present disclosure but do not limit the present disclosure.

EXAMPLES

All chemicals and DNA oligomers were obtained from commercially available sources and used without further purification. Protein MS analysis was performed using a Bruker Autoflex Speed MALDI-TOF mass spectrometer (Bruker Daltonics, Leipzig, Germany). All fluorescence spectra were obtained using the Hitachi F-7000 fluorescence spectrophotometer.

Screening of Aminoacyl-tRNA Synthetase Mutants (DOPA-RS1, DOPA-RS2)

A mutant gene library of *Methanococcus jannaschii* TyrRS (MjTyrRS) was obtained by overlapping PCR using pBK-DOPA-RS as a template and randomized sequences (NNK) and DNA primers at Asp158 and Ala167. The PCR product was cut with PST1 and EcoR1 and bonded to a pBK vector cut with the same restriction enzymes. A plasmid DNA containing the mutant gene library was transformed into DH10B electrocompetent cells containing pREP which has a chloramphenicol acetyltransferase (CAT) gene with an amber mutation at position Asp112. Transformants were cultured in an LB medium containing kanamycin and tetracycline, and cells were harvested after 12 hours of culture. The cells (2 mL) were transferred to a glycerol minimal medium (100 mL) containing kanamycin (50 μg/mL), tetracycline (12.5 μg/mL), 100 μM DTT, 1 mM L-DOPA, and chloramphenicol (35 μg/mL). The selective medium was cultured at 230 rpm, 37° C. for 16 hours. Surviving cells were diluted in an agar plate containing kanamycin and tetracycline, and pBK plasmids were isolated from colonies and characterized by sequencing.

Expression and Purification of Mutant Protein Containing L-DOPA

A wild-type emGFP gene was obtained from commercially available sources by gene synthesis, amplified by PCR, and inserted between the BspHI and KpnI sites of pBAD/Myc-His (Invitrogen) to generate pBAD-emGFP (SEQ ID NO: 10). An amber codon (TAG) was incorporated at position 39 or 90 in the emGFP by site-specific mutants. A plasmid containing each amber codon was incorporated into *E. coli* DH10 used as a prokaryote host cell with pEvol-DOPA-RS1 (SEQ ID NO: 6), pEvol-DOPA-RS2 (SEQ ID NO: 7), or pEvol-DOPA-RS (SEQ ID NO: 8) to co-transform the *E. coli* DH10 (Comparative Example 1: DOPA-RS1, Example 1: DOPA-RS1, Example 2: DOPA-RS2). Cells were amplified in an LB medium (lysogeny broth) supplemented with ampicillin (100 μg/mL) and chloramphenicol (35 μg/mL). The starter culture (2 mL) was transferred to a limiting medium (100 mL) (50 mM $Na_2HPO_4$, 50 mM $KH_2PO_4$, 50 mM $(NH_4)_2SO_4$, 2 mM $MgSO_4$, 0.1% trace metals, 0.5% glycerol, 0.05% glucose, and 5% amino acids) supplemented with ampicillin (100 μg/mL), chloramphenicol (35 μg/mL), 300 μM DTT, and 3 mM L-DOPA at 37° C. Protein expression was induced by adding 0.2% L-arabinose when the optical density reached 0.8, and the culture was cultured overnight at 37° C. Cells were harvested by centrifugation, resuspended in a lysis buffer (50 mM $Na_2HPO_4$, 300 mM NaCl, 10 mM imidazole, and pH 8.0) and sonicated. Target proteins were purified by Ni-NTA affinity chromatography under basic conditions according to the manufacturer (Qiagen)'s protocol. Protein concentrations were calculated by measuring absorbance at 280 nm and using the calculated extinction coefficient ($2.2\times10^4$ $cm^{-1}M^{-1}$ for emGFP).

Genetic Incorporation of L-DOPA Biosynthesized from Catechol

The tyrosine phenol-lyase (TPL) gene was amplified from *Citrobacter freundii* genomic DNA (ATCC8090) as a primer including Nco1 and Pst1 restriction sites. The gene was inserted between the NcoI and PstI sites of a pHCE vector (addgene) to generate pHCE-TPL. The TPL gene including a proximal promoter and terminator sequences in pHCE-TPL was amplified into a primer including a BsrG1 restriction site. The gene was inserted into the BsrG1 site of pBAD/Myc-His (Invitrogen). The C-terminal hexahistidine-tagged emGFP-E90TAG gene was amplified from pBADemGFP-E90TAG by using a primer including BspHI and Kpn1 restriction sites and inserted between the Nco1 and KpnI sites of the same vector to generate pBAD-dual-TPL-emGFP-E90TAG (SEQ ID NO: 9). The plasmid was incorporated into *E. coli* DH10B used as a prokaryote host cell with pEvol-DOPA-RS2 to co-transform the *E. coli* DH10B, and the transformed cells were amplified in an LB medium supplemented with ampicillin (100 μg/mL) and chloramphenicol (35 μg/mL). The starter culture (2 mL) was transferred to a limiting medium (100 mL) (50 mM $Na_2HPO_4$, 50 mM $KH_2PO_4$, 50 mM $(NH_4)_2SO_4$, 2 mM $MgSO_4$, 0.1% trace metals, 0.5% glycerol, 0.05% glucose, and 5% amino acids, and pH 7.25) supplemented with ampicillin (100 μg/mL), chloramphenicol (35 μg/mL), 100 μM pyruvate, 10 mM catechol, and 300 μM DTT at 30° C. Protein expression was induced by adding 0.2% L-arabinose when the optical density reached 0.8, and the culture was cultured overnight at 30° C. Cells were harvested by centrifugation, resuspended in a lysis buffer (50 mM $Na_2HPO_4$, 300 mM NaCl, 10 mM imidazole, and pH 8.0) and sonicated. Target proteins were purified by Ni-NTA affinity chromatography under basic conditions according to the manufacturer (Qiagen)'s protocol. Protein concentrations were calculated by measuring absorbance at 280 nm and using the calculated extinction coefficient ($2.2\times10^4$ $cm^{-1}M^{-1}$ for emGFP).

Fluorescence Measurement of emGFP

Cells ($2\times10^9$) were harvested by centrifugation at 10,000 rpm and 4° C. for 5 minutes, and cell pellets were lysed for 1 hour with Bugbuster (Novagen) (50 μL) supplemented with benzonase (Sigma) (250 units/4). The cytolysate was removed by centrifugation at 13,000 rpm and 4° C. for 10 minutes, and the supernatant was directly used for fluorescence measurement. Fluorescence was measured at 510 nm with excitation at 487 nm.

MALDI-TOF MS Analysis

Protein (200 μg, final concentration 0.5 mg/mL) was lysed in a reaction buffer containing 50 mM Tris and 0.1% SDS at 37° C. for 12 hours, and the lysed peptides were desalted using a C-18 spin column. The desalted tryptic degradation product was mixed with α-cyano-4-hydroxycinnamic acid (CHCA) matrix (10 mg/mL in water containing 70% acetonitrile and 0.1% trifluoroacetic acid) at a ratio of 1:1 (v/v), followed by MS analysis.

Novel Aminoacyl-tRNA Synthetase (aaRS)

A conventional aaRS (DOPA-RS) for L-DOPA was identified by screening a mutant aaRS library and included the following mutants: Tyr32Leu, Ala67Ser, His70Asn, and Ala167Gln. The detailed analysis of mutants used in the conventionally screened aaRS library and the X-ray crystallographic structure of MjTyrRS (*Methanococcus jannaschii* TyrRS) including tyrosine showed that 6 residues were already selected from the conventional library and L-DOPA was similar in structure to tyrosine, and, thus, no residue for additional mutants is present. Instead, the researchers of the present disclosure selected some residues used for constructing the conventional library since some mutants in the conventional library are still highly likely to be unprocessed due to a large size of the library (about $10^9$ mutants). The X-ray crystallographic structure of MjTyrRS showed that Asp158 and Ala167 were close to 3-position of phenyl ring of tyrosine coupled to MjTyrRS. A small-size aaRS mutant library was prepared by randomizing two residues and screened by a reported method. These two novel mutants are referred to as DOPA-RS1 and DOPA-RS2 respectively and were identified by screening the library and include the following mutants: DOPA-RS1, Asp158Asp, Ala167Asn; DOPA-RS2, Asp158Asp, and Ala167Leu. The above-described two mutants showed that Asp158 was a mutant optimized for L-DOPA and Ala167 could be mutated for development.

Figure 1B:
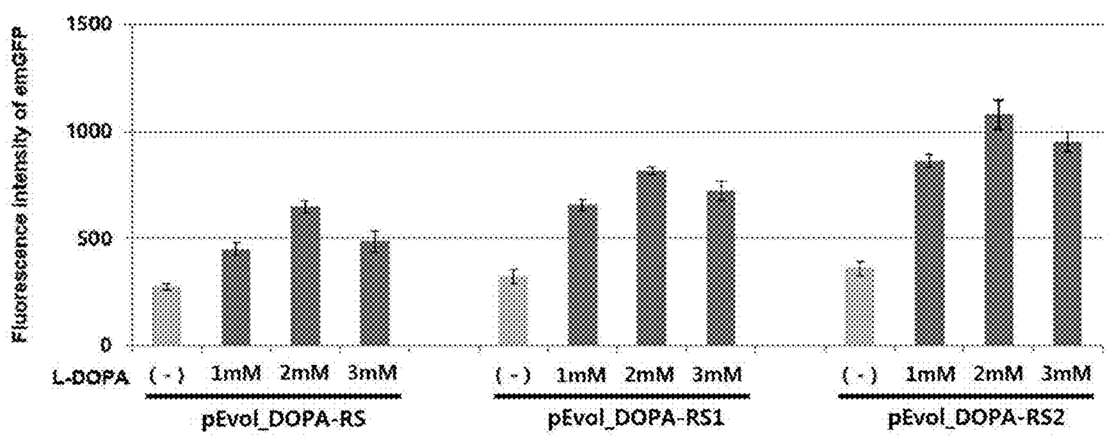
Figure 2:
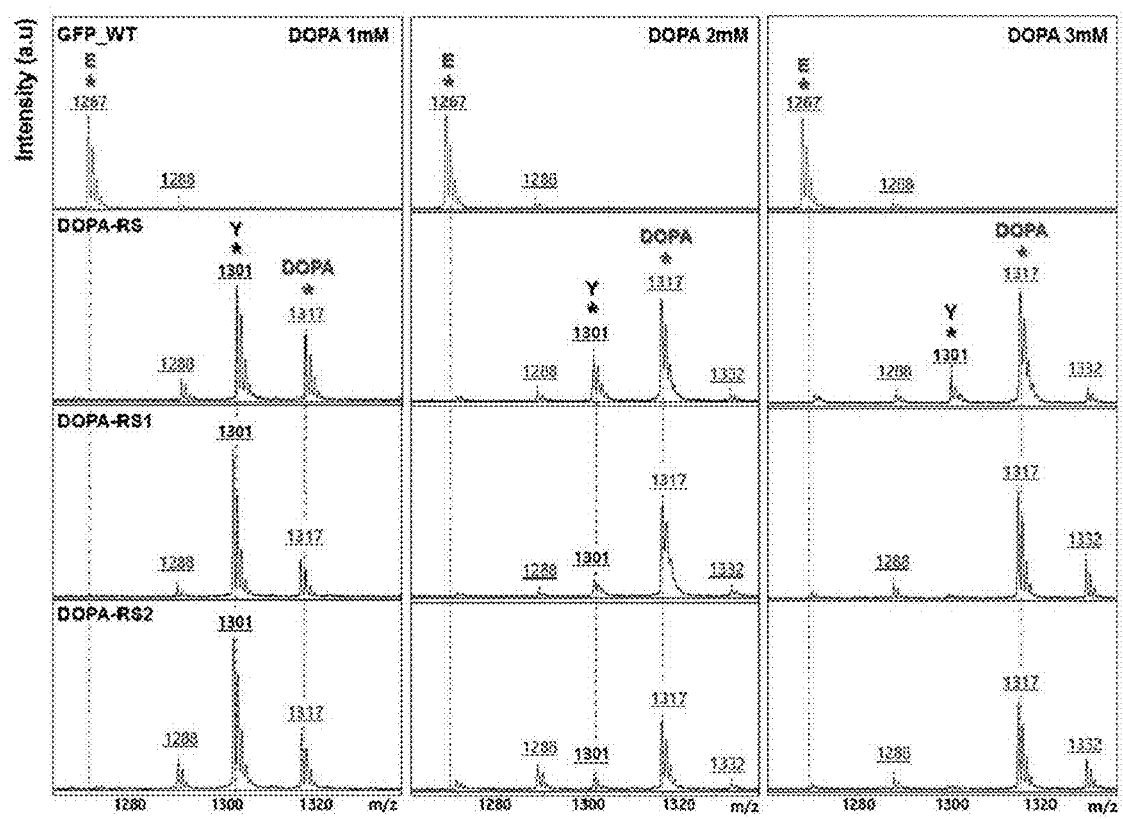
FIG. 2 provides graphs showing the result of MALDI-TOF MS analysis of emGFP-E90DOPA expressed by three aaRS mutants (Comparative Example 1: DOPA-RS, Example 1: DOPA-RS1, Example: DOPA-RS2) containing 1 mM, 2 mM, and 3 mM L-DOPA in an example of the present disclosure.

The identified mutant DOPA-RS1 or DOPA-RS2 was then evaluated in terms of efficiency and specificity of genetic incorporation of L-DOPA. The efficiency was tested by expressing emerald GFP (emGFP) containing an amber mutation (TAG) at position 39 or 90 in the presence of the novel aa-tRNA/DOPA-RS1 pair or aa-tRNA/DOPA-RS2 pair, 1 mM to 3 mM L-DOPA and measuring GFP fluorescence from the cytolysate. These tests were carried out using pEvol containing two aaRS genes (DOPA-RS1 and DOPA-RS2), and the system showed a higher efficiency in incorporation of L-DOPA than a system using pSup containing 6 copies of tRNA genes and an aaRS gene. The result of emGFP expression showed that the efficiency in incorporation of L-DOPA by three aaRS mutants was high in order of DOPA-RS2>DOPA-RS1>DOPA-RS at all L-DOPA concentrations and the two positions (FIG. 1). The incorporation of L-DOPA into the position 39 (FIG. 1A) showed emGFP fluorescence two times higher than the incorporation of L-DOPA into the position 90 (FIG. 1B). The intensity of fluorescence was increased as the concentration was increased from 1 mM to 2 mM, and in 3 mM L-DOPA, the cell density was partially decreased due to the toxicity of dopaquinone caused by oxidation of L-DOPA and the intensity of fluorescence for the same amount of cells was also decreased. In order to express an emGFP-E90DOPA mutant, the expressed protein was purified, followed by tryptic degradation and then evaluated by MALDI-TOF (matrix-assisted laser desorption/ionization-time of flight) MS analysis (FIG. 2). In FIG. 2, peptide E (residue 86-96; SAMPEGYVQER; SEQ ID NO: 11) is a tryptic peptide fragment containing 90 residues generated by trypsin digestion and peptide Y and peptide DOPA contain tyrosine and L-DOPA at position 90. The MS analysis on the mutant protein expressed by 1 mM L-DOPA showed the incorporation of a large amount of tyrosine into all of three aaRS mutants. However, the mutant protein expressed by 2 mM L-DOPA showed the incorporation of L-DOPA in excess by 70% of DOPA-RS and in excess by 90% of DOPA-RS1 and DOPA-RS2. In 3 mM L-DOPA, the incorporation of tyrosine was still observed in the case of expression by DOPA-RS (incorporation of about 10% tyrosine), but the incorporation of tyrosine was not detected in the case of expression by DOPA-RS1 and DOPA-RS2. This result means that the novel aaRS (DOPA-RS1 and DOPA-RS2) of the present disclosure had an improved accuracy in incorporation of L-DOPA. Tyrosine and L-DOPA compete with each other due to their structural similarity. In order for L-DOPA to be dominant in the competition, a protein in which only biosynthesized L-DOPA is purely incorporated without incorporation of tyrosine needs to be expressed and purified, as shown in FIG. 1 in which the biosynthesized L-DOPA has a concentration of 3 mM or more. Therefore, the above-described result confirms that when the novel aaRS (DOPA-RS1 and DOPA-RS2) of the present disclosure is used, a biosynthesized L-DOPA is required to have a concentration of 3 mM or more for genetic incorporation without incorporation of tyrosine.

Selection of Target Enzyme for L-DOPA Biosynthesis

A commercially available L-DOPA is mainly produced by chemical synthesis using an asymmetric reaction such as asymmetric hydrogenation. However, this process requires expensive metal catalysts and difficult reaction conditions and often results in unsatisfactory yield and enantioselectivity. As an alternative process, enzyme synthesis has been developed and used to produce a commercially available L-DOPA. Enzymes used for this purpose include tyrosine phenol-lyase (TPL) and p-hydroxyphenylacetate 3-hydroxylases (PHAH). The catalytic reactions catalyzed by these enzymes were considered as target reactions for L-DOPA biosynthesis. One thing to consider for selection of a target enzyme for L-DOPA biosynthesis is that the novel aaRS mutant incorporates tyrosine and L-DOPA competes with tyrosine for a substrate of the aaRS mutant. Among the above-described enzymes, tyrosinase and PHAHs use tyrosine as a substrate for L-DOPA biosynthesis. Therefore, high density tyrosine is an important requirement for genetic incorporation of biosynthesized L-DOPA and cannot be compatible with the substrate selectivity of the aaRS mutant. TPL which is another enzyme can catalyze degradation of tyrosine into phenol, pyruvate, and ammonia. This enzymatic reaction is known as being in equilibrium, and the reverse reaction is catalyzed to form tyrosine in the presence of phenol, pyruvate, and ammonia. Further, it has been reported that if phenol is substituted with catechol, L-DOPA can be synthesized by TPL. Therefore, TPL was selected as a target enzyme for L-DOPA biosynthesis from catechol, pyruvate, and ammonia.

Optimization of Biosynthesis Conditions for L-DOPA

Figure 3:
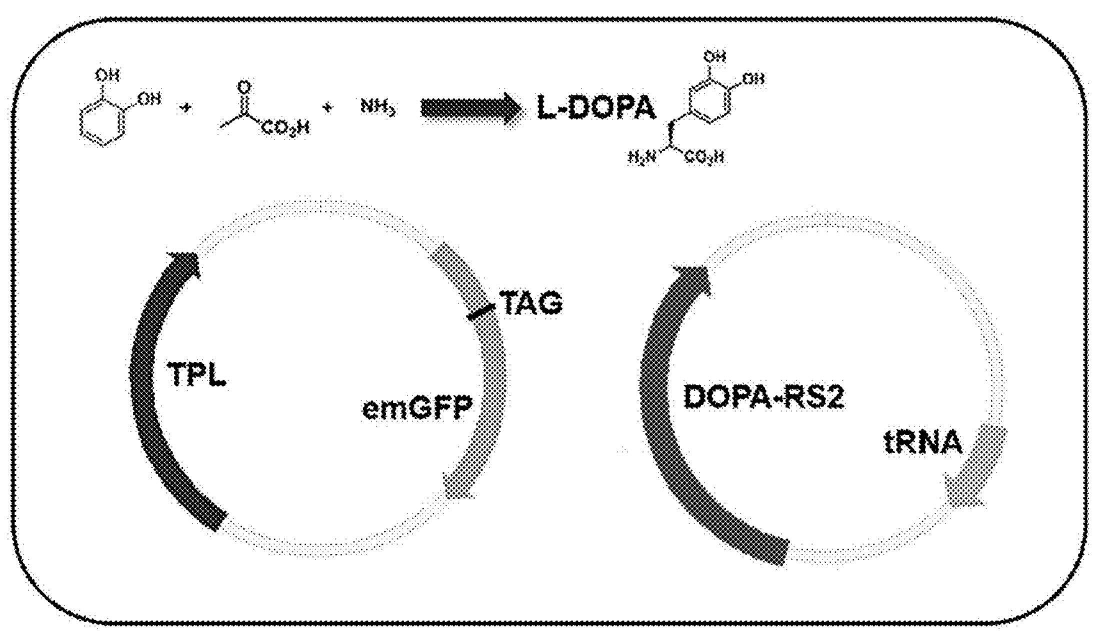
FIG. 3 shows a direct incorporation system of L-DOPA biosynthesized from tyrosine phenol-lyase (TPL) in an example of the present disclosure.
Figure 4:
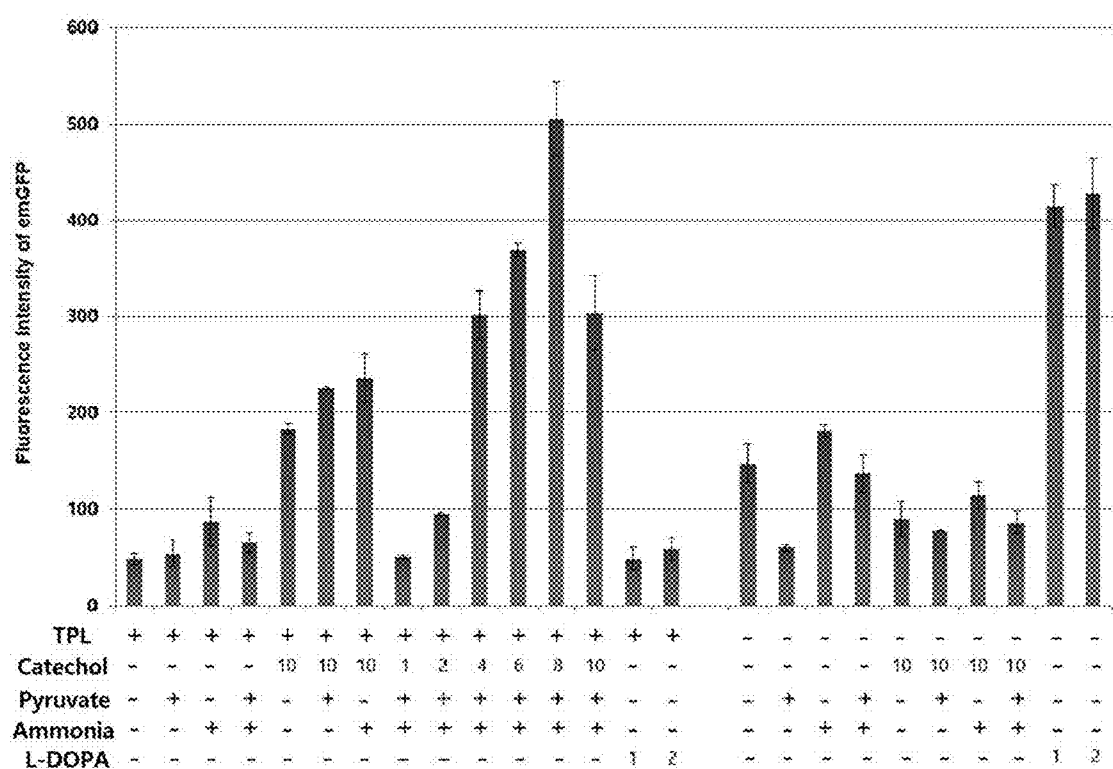
FIG. 4 is a graph showing fluorescence measured from emGFP-E90DOPA expressed by L-DOPA biosynthesized from TPL in an example of the present disclosure.
Figure 5:
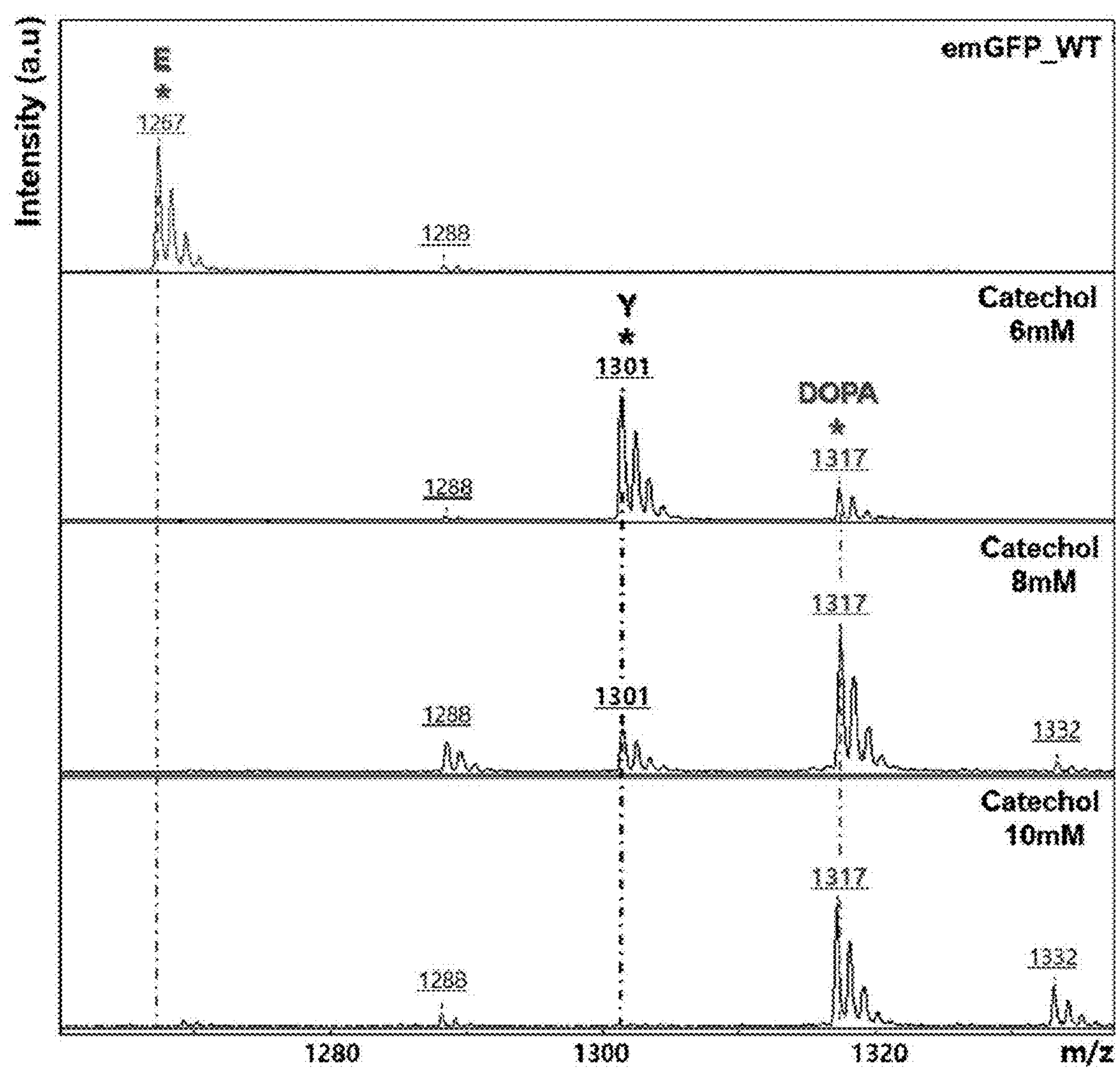
FIG. 5 is a graph showing the result of MALDI-TOF MS analysis of emGFP-E90DOPA expressed by L-DOPA biosynthesized from TPL in the presence of 6 to 10 mM catechol, 50 mM pyruvate, and 25 mM ammonium sulfate in an example of the present disclosure.

Although TPL was used for L-DOPA biosynthesis, the conditions reported in the literature could not be compatible with direct genetic incorporation of a biosynthesized L-DOPA into a target protein. In order to maximize the yield of L-DOPA biosynthesis, the reaction equilibrium in an L-DOPA synthesis reaction needs to be shifted from catechol, pyruvate, and ammonia toward the formation of L-DOPA using a catalyst TPL. A simple solution was to maximize the concentrations of catechol, pyruvate, and ammonia in a growth medium. However, in a preliminary test, a concentration of catechol of more than 8 mM inhibited bacterial cell growth and concentrations of pyruvate and ammonia of more than 50 mM and more than 25 mM, respectively, did not affect the biosynthesis of L-DOPA. Based on these results, an emGFP gene containing an amber mutation at position 90 was expressed as expression of aa-tRNA/DOPA-RS2 pair and TPL as shown in FIG. 3. In the growth medium, 50 mM pyruvate and 25 mM ammonia were added as starting materials together with various concentrations (0 mM to 10 mM) catechol. The result showed that the expression of emGFP was increased until the concentration of catechol was increased to 8 mM, and the expression of emGFP was slightly decreased at 10 mM due to toxicity of catechol (FIG. 4). The expression of emGFP showed a higher intensity when 8 mM catechol was used as compared with a control test using 1 mM L-DOPA and 2 mM L-DOPA. The same control test including the expression of L-DOPA and TPL showed a low expression of emGFP because TPL degraded L-DOPA into catechol, pyruvate, and ammonia. Another control test in which pyruvate and ammonia were removed showed that the effect of pyruvate or ammonia on L-DOPA biosynthesis was not significant under these conditions because ammonium sulfate (25 mM) and the growth medium containing pyruvate were present in the bacterial cells. In order to verify the incorporation of biosynthesized L-DOPA from catechol, pyruvate, and ammonia, the expressed emGFP was purified, followed by tryptic degradation and then analyzed by MALDI-TOF (matrix-assisted laser desorption/ionization-time of flight) MS. The incorporation of tyrosine was observed from degraded peptides generated from the expressed emGFP in the presence of 8 mM catechol or less (FIG. 5). However, with 10 mM catechol, L-DOPA was exclusively incorporated without incorporation of tyrosine. The L-DOPA and tyrosine compete with each other due to their structural similarity. Therefore, in order to increase the incorporation rate of L-DOPA, a protein a protein in which only biosynthesized L-DOPA is purely incorporated without incorporation of tyrosine needs to be expressed and purified. Therefore, this result showed that the incorporation rate of L-DOPA biosynthesized by TPL was similar to the efficiency of 3 mM L-DOPA shown in FIG. 1. When 10 mM catechol was administered, a reasonable toxicity was observed. However, this result showed that since tyrosine was not incorporated, L-DOPA could be incorporated with more efficiency. Further, the cell density obtained under these conditions was much higher than that with 3 mM L-DOPA, which shows that the yield of protein obtained by biosynthesis was much higher than that with 3 mM L-DOPA (FIG. 6).

Figure 6A:
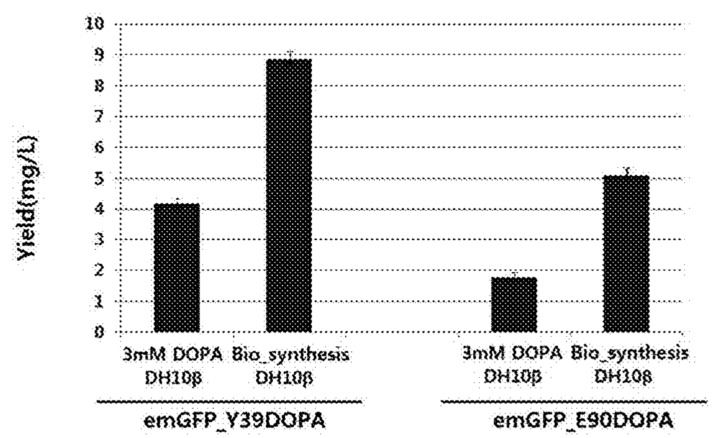
FIGS. 6A, 6B and 6C provide graphs comparing general genetic incorporation of L-DOPA with direct incorporation of L-DOPA biosynthesized from TPL in an example of the present disclosure.

FIG. 6 compares general genetic incorporation of L-DOPA (conventional gene incorporation system) with direct incorporation of L-DOPA (using DOPA-RS1 or DOPA-RS2) biosynthesized from TPL according to the present disclosure. In FIG. 6A, "3 mM DOPA DH1013" represents the yield of protein when only 3 mM DOPA was incorporated without biosynthesis and "Biosynthesis DH10β" represent the yield of protein when the protein was incorporated with L-DOPA biosynthesis according to the present disclosure (DH10β: Bacterial strain name). As shown in FIG. 6A, it can be seen that the system (Biosynthesis DH10β) using the biosynthesis and incorporation method of the present disclosure has a much higher yield of protein than Comparative Example (3 mM DOPA DH10β) in which only L-DOPA was incorporated without biosynthesis.

Figure 6B:
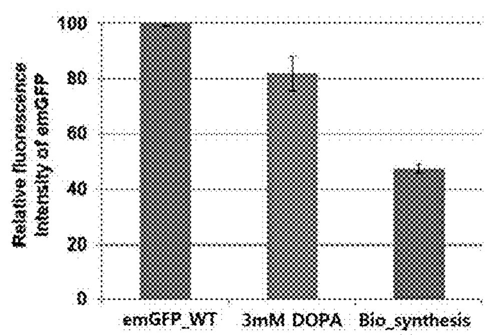
Figure 6C:
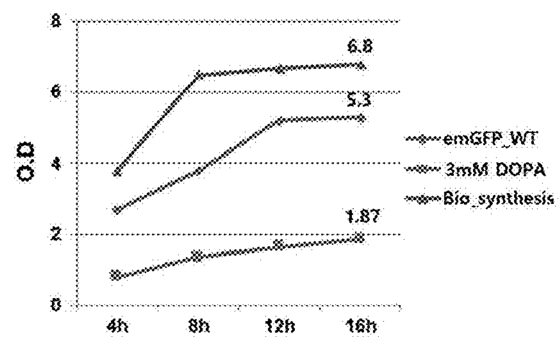

FIG. 6B and FIG. 6C support the result shown in FIG. 6A, and compare emGFP fluorescence (FIG. 6B) and cell density (FIG. 6C) among a wild-type control (emGFF_WT) as a reference respectively, the example where only 3 mM DOPA was incorporated without biosynthesis (3 mM DOPA), and the biosynthesis system (Biosynthesis) according to the present disclosure. The biosynthesis system according to the present disclosure has a lower relative fluorescence intensity than the control (emGFP_WT), but as shown in FIG. 6C, an O.D value measured from the biosynthesis introduction system according to the present disclosure was as high as 6.8 despite the lower fluorescence intensity. As a result, it can be seen that the novel incorporation system of the present disclosure has a higher incorporation rate.

Conjugation using SPOCQ reaction of protein in which L-DOPA is genetically incorporated DOPA can be oxidized to L-dopaquinone that reacts with strained cyclooctynes and nucleophiles such as amines and thiols, and can be used as a bioorthogonal handle for protein conjugation.

Figure 7A:
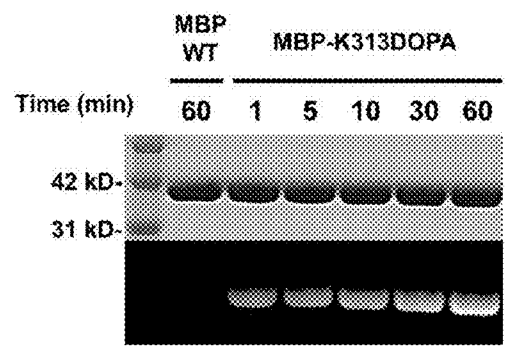
FIGS. 7A and 7B show protein conjugation by SPOCQ cycloaddition reactions of MBP-K313DOPA and ADIBOCy5.5 in an example of the present disclosure.
Figure 7B:
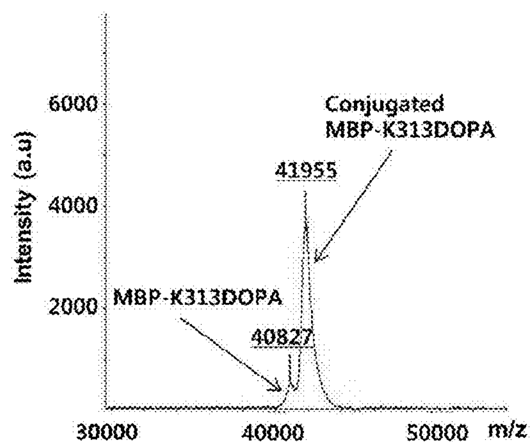

In order to verify the incorporation of DOPA biosynthesized from the TPL and the applicability of protein conjugation, the DOPA was incorporated into a maltose binding protein (MBP). A MBP gene containing an amber mutation at position 313, a TPL gene, and an aatRNA/DOPA-RS2 gene were expressed in the presence of catechol, pyruvate, and ammonia. The expressed MBP (MBP-K313DOPA) containing DOPA was purified by affinity chromatography and tested for SPOCQ (strain-promoted oxidation controlled cyclooctyne-1,2-quinone) cycloaddition reaction. The MBP-K313DOPA was treated with sodium periodate to generate L-dopaquinone and the generated L-dopaquinone was reacted with a Cy5.5-ADIBO (Cy5.5-linked azadibenzocyclooctyne). The cycloaddition reaction was analyzed by SDS-PAGE and fluorescence imaging (FIG. 7A). In the SDS-PAGE, the gel was visualized by Coomassie staining and fluorescence. The reaction was analyzed for 60 minutes and the reaction product increased over time. If reacted with WT MBP similarly or not treated with sodium periodate, it did not show fluorescence within 60 minutes, which verified the specificity of conjugation with the genetically incorporated DOPA (FIG. 7A and FIG. 7B).

The conjugation efficiency for the MBP-K313DOPA reacted with ADIBO-Cy5.5 for 60 minutes was also analyzed by MALDI-TOF MS. An estimated mass difference between the MBP-K313DOPA and the conjugation protein was 1151 Da, and the actually observed mass difference was 1128 Da. The MALDI-TOF MS analysis showed the efficient conjugation of the MBP-K313DOPA and the Cy5.5-ADIBO (85% to 90% of the integral value of MS peaks). The genetically incorporated DOPA had not been used for SPOCQ cycloaddition reaction before. Therefore, the conjugation method of the present disclosure can be a great alternative to other protein conjugation methods.

Synthesis of Oligomeric Protein

Figure 8:
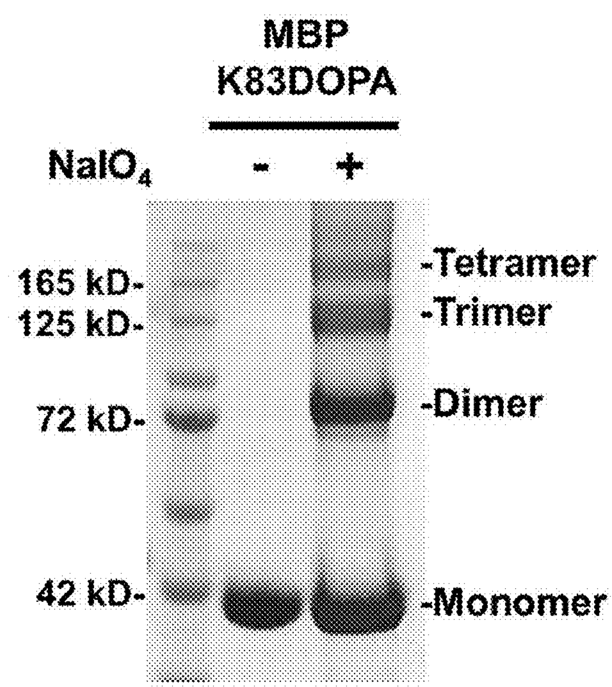
FIG. 8 shows the oligomerization of MBP-K83DOPA in an example of the present disclosure.

The inventors of the present disclosures observed that purified MBP containing DOPA produced oligomeric proteins after it was stored in a phosphate buffer for a few days. The oligomerization is presumed as a result of oxidation of the DOPA in the protein to L-dopaquinone by oxygen dissolved in the buffer and nucleophilic attack of L-dopaquinone caused by lysine on the MBP surface. To confirm this, the mutant protein, MBP-K83DOPA, was treated with sodium periodate and cultured for 48 hours and then analyzed by SDS-PAGE through comparison with an untreated sample (FIG. 8). The analysis showed that non-oligomerized proteins were observed in the untreated sample, whereas a clear oligomerization pattern was observed in the periodate-treated sample. The characteristics of the oligomer were not further analyzed, but in consideration of the number of lysines (36 lysines) in the MBP, the reaction was presumed to be nonspecific. This oligomerization could be suppressed by adding a reducing agent such as dithiothreitol to the storage buffer.

Protein-Protein Cross-Linking

Genetically encoded DOPA was also used to capture protein-protein interactions by covalent bond formation. Previous studies disclosed a model system conjugated by an electrophilic amino acid in which an affibody and its binding partner were genetically incorporated.

Figure 9:
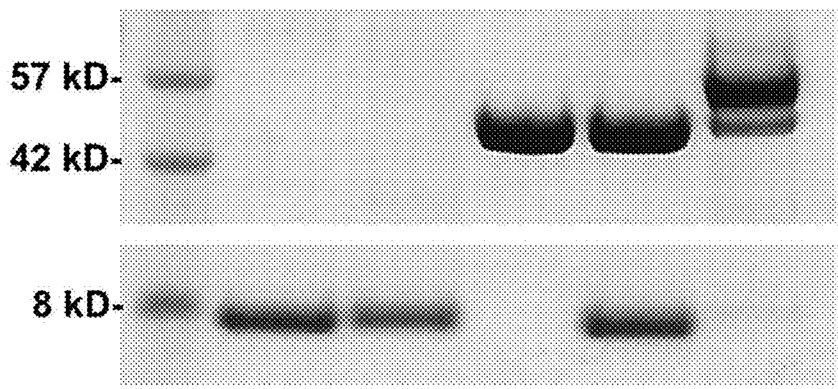
FIG. 9 shows the cross-linking of AFB-D36DOPA and MBP-Z-N6K in an example of the present disclosure.

In the present disclosure, DOPA was biosynthesized and genetically incorporated into position 36 of the ZSPA affibody (AFB), and Asn6 mutated into Lys in a Z-domain protein which is a binding partner of the affibody. The Z-domain gene was fused with MBP (MBP-Z) to differentiate the protein from the AFB in SDS-PAGE analysis. AFBD36DOPA and MBP-Z-N6K were expressed, purified, and tested for protein cross-linking. The AFBD36DOPA was treated with sodium periodate and reacted with MBP-Z-N6K for 4 hours, and the mixture was analyzed by SDS-PAGE (FIG. 9). Cross-linking was not observed in the MBP-ZN6K reacted with AFB-WT, whereas the crosslinking of the AFBD36DOPA and the MBP-Z-N6K was efficient with 70% to 75% of cross-linked products. The proximity-enabled protein-protein cross-linking using the genetically encoded DOPA had a higher efficiency than the conventional system using unnatural amino acids including alkyl halides.

In conclusion, L-DOPA was biosynthesized from starting materials including catechol, pyruvate, and ammonia by using a TPL, and the biosynthesized amino acid was directly incorporated into proteins by co-expression corresponding to a pair of the novel aaRS (DOPA-RS1 or DOPA-RS2) and aminoacyl-tRNA of the present disclosure. The DOPA-RS1 or DOPA-RS2 as the novel aaRS of the present disclosure used for the incorporation of L-DOPA was selected from the aaRS library and showed a higher efficiency than the previously reported original aaRS (DOPA-RS). The direct incorporation system showed the efficient incorporation of L-DOPA without incorporation of tyrosine and a higher protein yield than the conventional incorporation system using L-DOPA. Therefore, mutant proteins containing L-DOPA can be produced at reduced cost (to less than 10%) and improved yield (to more than 200%) by using the system for directly incorporating L-DOPA into the target protein by the pair of the novel aaRS and aatRNA. This approach can be useful for mass production of proteins for pharmaceutical and industrial application and can provide an impetus for expansion of biosynthesis of unnatural amino acids to more challenging and interesting amino acids.

In the present disclosure, an L-DOPA was biosynthesized using by a tyrosine phenol-lyase (TPL) starting from catechol, pyruvate, and ammonia in *Escherichia coli*, and the biosynthesized amino acid was directly incorporated into target proteins by genetic incorporation using a pair of a novel aminoacyl-tRNA synthetase (aaRS) and aminoacyl-tRNA (aa-tRNA). Firstly, the efficiency and accuracy of the aaRS in genetic incorporation of an L-DOPA was adjusted by screening the aaRS mutant library. The novel DOPA-RS1 or DOPA-RS2 as the aaRS used for the incorporation of an L-DOPA was selected from the aaRS library and showed a higher efficiency than the previously reported original aaRS (DOPA-RS). Then, a biosynthesis system using the TPL for biosynthesis of an L-DOPA in cells was constructed, and the biosynthesized L-DOPA was directly incorporated into the target proteins. This direct incorporation system showed the efficient incorporation of an L-DOPA without incorporation of tyrosine and a higher protein yield than the conventional incorporation system using an L-DOPA. Therefore, mutant proteins containing an L-DOPA can be produced at reduced cost and improved yield by using the biosynthesis system. This method is useful for mass production of proteins for pharmaceutical and industrial application and can provide an impetus for expansion of biosynthesis of unnatural amino acids to more challenging and interesting amino acids. In consideration of successful incorporation of an L-dihydroxyphenylalanine into target proteins using *E. coli*, a kind of prokaryote, in one example of the present disclosure, the L-dihydroxyphenylalanine can be successfully incorporated into target proteins even when another prokaryote is used instead of *E. coli*.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A method of genetically incorporating an L-dihydroxyphenylalanine in a target protein, comprising:

genetically incorporating an expression vector including a gene of SEQ ID NO: 1 or SEQ ID NO: 2 into a prokaryote to obtain a transformant;

culturing the transformant in a medium so that the prokaryote biosynthesizes L-dihydroxyphenylalanine (L-DOPA) and the biosynthesized L-dihydroxyphenylalanine is incorporated into a target protein contained in the prokaryote; and separating or purifying the L-dihydroxyphenylalanine-incorporated target protein from the prokaryote.

2. The method of genetically incorporating an L-dihydroxyphenylalanine in a target protein of claim 1, wherein the incorporation of the L-dihydroxyphenylalanine into the target protein is performed by an aminoacyl-tRNA synthetase (aaRS) and an aminoacyl-tRNA (aa-tRNA), wherein the aminoacyl-tRNA synthetase (aaRS) is an aaRS of SEQ ID NO: 3 and the aminoacyl-tRNA (aa-tRNA) is an aa-tRNA of SEQ ID NO: 5, or by the aminoacyl-tRNA synthetase (aaRS) of SEQ ID NO: 4 and the aminoacyl-tRNA (aa-tRNA) of SEQ ID NO: 5.

3. The method of genetically incorporating an L-dihydroxyphenylalanine in a target protein of claim 1, further comprising genetically incorporating an expression vector including the target protein into the prokaryote, wherein the target protein includes a member selected from the group consisting of a green fluorescent protein (GFP), an emerald green fluorescent protein (emGFP), an enhanced green fluorescent protein (eGFP), a maltose-binding protein (MBP), and combinations thereof.

4. The method of genetically incorporating an L-dihydroxyphenylalanine in a target protein of claim 1, wherein the prokaryote[s] includes a member selected from the group consisting of *Escherichia* genus, *Serratia* genus, *Corynebacterium* genus, *Brevibacterium* genus, *Pseudomonas* genus, *Bacillus* genus, *Microbacterium* genus, and combinations thereof.

5. The method of genetically incorporating an L-dihydroxyphenylalanine in a target protein of claim 1, wherein the medium includes catechol, pyruvate, and ammonia.

6. A method of genetically incorporating an L-dihydroxyphenylalanine in a target protein, comprising:

genetically incorporating an expression vector including a gene encoding SEQ ID NO: 3 or SEQ ID NO: 4 into a prokaryote to obtain a transformant;

culturing the transformant in a medium so that the prokaryote biosynthesizes L-dihydroxyphenylalanine (L-DOPA) and the biosynthesized L-dihydroxyphenylalanine is incorporated into a target protein contained in the prokaryote; and separating or purifying the L-dihydroxyphenylalanine-incorporated target protein from the prokaryote.

* * * * *